(12) United States Patent
Dixit

(10) Patent No.: US 7,097,972 B1
(45) Date of Patent: Aug. 29, 2006

(54) METHOD AND COMPOSITION FOR REGULATING APOPTOSIS

(75) Inventor: Vishva M. Dixit, Ann Arbor, MI (US)

(73) Assignee: Regents of the University of Michigan, Ann Arbor, MI (US)

(*) Notice: Subject to any disclaimer, the term of this patent is extended or adjusted under 35 U.S.C. 154(b) by 571 days.

(21) Appl. No.: 08/457,731

(22) Filed: Jun. 1, 1995

Related U.S. Application Data

(63) Continuation-in-part of application No. 08/389,812, filed on Feb. 13, 1995.

(51) Int. Cl.
  *C12Q 1/68* (2006.01)
  *C12N 15/00* (2006.01)
  *C12N 5/08* (2006.01)
  *C07H 21/04* (2006.01)

(52) U.S. Cl. .................. 435/6; 435/320.1; 435/371; 435/372.2; 536/23.5; 536/25.3

(58) Field of Classification Search ................ 536/23.1, 536/23.5, 25.3; 514/44; 435/240.2, 6, 320.1, 435/371, 372.2; 424/93.1
See application file for complete search history.

(56) References Cited

U.S. PATENT DOCUMENTS

| 4,107,297 A | 8/1978 | Omura et al. ............... 424/122 |
| 4,683,195 A | 7/1987 | Mullis et al. .................. 435/6 |
| 4,683,202 A | 7/1987 | Mullis .......................... 435/91 |
| 4,754,065 A | 6/1988 | Levenson et al. ........... 562/564 |
| 4,800,159 A | 1/1989 | Mullis et al. ............ 435/172.3 |
| 5,258,454 A | 11/1993 | Berg et al. ................ 525/54.11 |
| 5,674,734 A | 10/1997 | Leder et al. ............. 435/252.3 |
| 6,060,238 A * | 5/2000 | Dixit |
| 6,087,150 A * | 7/2000 | He et al. |

FOREIGN PATENT DOCUMENTS

| WO | WO 93/25694 | 12/1993 |
| WO | WO 94/18317 | 8/1994 |
| WO | WO 94/21817 | 9/1994 |
| WO | WO 94/24297 | 10/1994 |
| WO | WO 94/25621 | 11/1994 |
| WO | WO 94/27583 | 12/1994 |
| WO | WO 95/31544 | 11/1995 |
| WO | WO 96/01642 | 1/1996 |
| WO | WO 96/18641 | 6/1996 |
| WO | WO 96/20721 | 7/1996 |
| WO | WO 96/25945 | 8/1996 |
| WO | WO 96/36698 | 11/1996 |
| WO | WO 96/40713 | 12/1996 |
| WO | WO 97/03998 | 2/1997 |
| WO | WO 97/18313 | 5/1997 |
| WO | WO 98/103648 | 1/1998 |

OTHER PUBLICATIONS

Tomei et al., Apoptosis: The Molecular Basis of Cell Death (1991) Cold Spring Harbor Press, New York. A title page and table of contents were previously submitted.
Tomei et al., Apoptosis II: The Molecular Basis of Cell Death (1994) Cold Spring Harbor Press, New York. A title page and table of contents were previously submitted.
Duvall et al., "Death and the cell" Immunol. Today (1986) 7:115–119.
Dhein et al., "Autocrine T–cell suicide mediated by APO–1/(Fas/CD95)" Nature (1995) 373:438–441.
Brunner et al., "Cell–autonomous Fas (CD95)/Fas–ligand interaction mediates activation–induced apoptosis in T–cell hybridomas" Nature (1995) 373:441–444.
Ju et al., "Fas(CD95)/FasL interactions required for programmed cell death after T–cell activation" Nature (1995) 373:444–448.
Spriggs et al., "Tumor necrosis factor expression in human epithelial tumor cell lines" J. Clin. Invest. (1988) 81:455–460.
Watanabe–Fukunaga et al., "The cDNA structure, expression, and chromosomal assignment of the mouse Fas antigen" J. Immun. (1992) 148:1274–1279.
Owen–Schaub et al., "Anti–Fas on nonhematopoietic tumors: Levels of Fas/APO–1 and bcl–2 are not predictive of biological responsiveness" Cancer Res. (1994) 54:1580–1586.
Opipari, Jr. et al., "The A20 zinc finger protein protects cells from tumor necrosis factor cytotoxicity" J. Biol. Chem. (1992) 267:12424–12427.
Yonehara et al.. "A cell–killing monoclonal antibody (ANTI–Fas) to a cell surface antigen co–downregulated with the receptor of tumor necrosis factor" J. Exp. Med. (1989) 169:1747–1756.
Pickup et al., "Hemorrhage in lesions caused by cowpox virus is induced by a viral protein that is related to plasma protein inhibitors of serine proteases" Proc. Natl. Acad. Sci. (1986) 83:7698–7702.

(Continued)

*Primary Examiner*—Terry Mickelvey
*Assistant Examiner*—Maria Marvich
(74) *Attorney, Agent, or Firm*—Medlen & Carroll, LLP

(57) ABSTRACT

This invention provides non-naturally occurring and isolated naturally occurring nucleic acid molecules which encode proteins designated pro-Yama, p11 Yama and p20 Yama. This invention also provides recombinant polynucleotides coding for these proteins. Also provided by this invention is a non-naturally occurring nucleic acid molecule encoding mutant CrmA protein and a dominant inhibitory Yama. Vectors and host cells containing these nucleic acid molecules are further provided. Methods of modulating a cellular function regulated by the Fas receptor pathway in a cell is provided herein. In one aspect, this method comprises introducing into the cell a nucleic acid molecule coding for a gene product having CrmA biological activity such as dominant inhibitory Yama or alternatively, the CrmA gene product.

3 Claims, 14 Drawing Sheets

OTHER PUBLICATIONS

Miller et al., "Improved retroviral vectors for gene transfer and expression" BioTechniques (1989) 7:980–990.

Correll et al., "Production of human glucocerebrosidase in mice after retroviral gene transfer into multipotential hematopoietic progenitor cells" Proc. Natl. Acad. Sci. USA (1989) 86:8912–8916.

Bordignon et al., "Retroviral vector–mediated high–efficiency expression of adenosine deaminase (ADA) in hematopoietic long–term cultures of ADA–deficient marrow cells" Proc. Natl. Acad. Sci. USA (1989) 86:6748–6752.

Culver et al., "Lymphocytes as cellular vehicles for gene therapy in mouse and man" Proc. Natl. Acad. Sci. USA (1991) 88:3155–3159.

Rill et al., "An approach for the analysis of relapse and marrow reconstitution after autologous marrow transplantation using retrovirus–mediated gene transfer" Blood (1992) 79:2694–2700.

Anderson, "Human gene therapy" Science (1992) 256:808–813.

Ray et al., "Viral inhibition of inflammation: Cowpox virus encodes an inhibitor of the interleukin–1β converting enzyme" Cell (1992) 69:597–604.

Moss, "Poxviridae and their reproduction" Virology, 2nd ed., Fields, B.N. et al., eds., Raven Press, New York (1990) Chapter 74, pp. 2079–2111.

Itoh et al., "The polypeptide encoded by the cDNA for human cell surface antigen Fas can mediate apoptosis" Cell (1991) 66:233–243.

Laherty et al. "Human T cell leukemia virus Type I tax and phorbol 12–myristate 13–acetate induce expression of the A20 zinc finger protein by distinct mechanisms involving nuclear factor KB" J. Biol. Chem. (1993) 268:5032–5039.

Lum et al., "Coactivation with anti–CD28 monoclonal antibody enhances anti–CD3 monoclonal antibody–induced proliferation and IL–2 synthesis in T cells from autologous bone marrow transplant recipients" Bone Marrow Transplantation (1993) 12:565–571.

Tartaglia et al., "A novel domain within the 55 kd TNF receptor signals cell death" Cell (1993) 74:845–853.

Dixit et al., "Tumor necrosis factor–α induction of novel gene products in human endothelial cells including a macrophage–specific chemotaxin" J. Biol. Chem. (1990) 265:2973–2978.

Barres et al., "Cell death and control of cell survival in the oligodendrocyte lineage" Cell (1992) 70:31–46.

Boudreau et al., "Suppression of ICE and apoptosis in mammary epithelial cells by extracellular matrix" Science (1995) 267:891–893.

Cerretti et al., "Molecular cloning of the interleukin–1β converting enzyme" Science (1992) 256:97–100.

Ellis et al., "Genetic control of programmed cell death in the nematode C. elegans" Cell (1986) 44:817–829.

Ellis et al., "Mechanisms and functions of cell death" Ann. Rev. Cell. Biol. (1991) 7:663–698.

Finkel et al., "Apoptosis occurs predominantly in bystander cells and not in productively infected cells of HIV– and SIV–infected lymph nodes" Nature Med. (1995) 1:129–134.

Gagliardini et al., "Prevention of vertebrate neuronal death by the crmA gene" Science (1994) 263:826–828.

Gooding, "Virus proteins that counteract host immune defenses" Cell (1992) 71:5–7.

Hanabuchi et al., "Fas and its ligand in a general mechanism of T–cell–mediated cytotoxicity" Proc. Natl. Acad. Sci. USA (1994) 91:4930–4934.

Itoh et al., "Effect of bcl–2 on Fas antigen–mediated cell death" J. Immunol. (1993) 151:621–627.

Itoh et al., "A novel protein domain required for apoptosis" J. Biol. Chem. (1993) 268:10932–10937.

Iwai et al., "Differential expression of bcl–2 and susceptibility to anti–Fas–mediated cell death in peripheral blood lymphocytes, monocytes, and neutrophils" Blood (1994) 84:1201–1208.

Ju et al., "Participation of target Fas protein in apoptosis pathway induced by CD4$^+$ Th1 and CD8$^+$ cytotoxic T cells" Proc. Natl. Acad. Sci. USA (1994) 91:4185–4189.

Kägi et al., "Fas and perforin pathways as major mechanisms of T cell–mediated cytotoxicity" Science (1994) 265:528–530.

King et al., "Signaling for death of lymphoid cells" Current Opinion in Immunol. (1993) 5:368–373.

Komiyama et al., "Inhibition of interleukin–1β converting enzyme by the cowpox virus serpin CrmA" J. Biol. Chem. (1994) 269:19331–19337.

Kumar et al., "Protection from tumor necrosis factor–mediated cytolysis by overexpression of plasminogen activator inhibitor type–2" J. Biol. Chem. (1991) 266:20960–20964.

Kumar et al., "Induction of apoptosis by the mouse Nedd2 gene, which encodes a protein similar to the product of the Caenorhabditis elegans cell death gene ced–3 and the mammalian IL–1β–converting enzyme" Genes & Devel. (1994) 8:1613–1626.

Martin et al., "Biochemical characterization of programmed cell death in NGF–deprived sympathetic neurons" J. Neurobiol. (1992) 23:1205–1220.

Pantaleo et al., "Apoptosis in HIV infection" Nature Med. (1995) 1:118–120.

Ruggiero et al., "Protection from tumor necrosis factor cytotoxicity by protease inhibitors" Cellular Immunol. (1987) 107:317–325.

Stalder et al., "Fas antigen is the major target nolecule for CD4$^+$ T cell–mediated cytotoxicity" J. Immunol. (1994) 152:1127–1133.

Strasser, "Death of a T cell" Nature (1995) 373:385–387.

Suffys et al., "Involvement of a serine protease in tumour–necrosis–factor–mediated 4 cytotoxicity" Eur. J. Biochem. (1988) 178:257–265.

Thornberry et al., "A novel heterodimeric cysteine protease is required for interleukin–1J processing in monocytes" Nature (1992) 356:768–774.

Trauth et al., "Monoclonal antibody–mediated tumor regression by induction of apoptosis" Science (1989) 245:301–305.

Vaux et al., "An evolutionary perspective on apoptosis" Cell (1994) 76:777–779.

Walker et al., "Crystal structure of the cysteine protease interleukin–1β–converting enzyme: A $(p20/p10)_2$ homodimer" Cell (1994) 78:343–352.

White, "Regulation of apoptosis by the transforming genes of the DNA tumor virus adenovirus (43631)" P.S.E.B.M. (1993) 204:30–39.

Wilson et al., "Structure and mechanism of interleukin–1β converting enzyme" Nature (1994) 370:270–275.

Yuan et al., "The C. elegans cell death gene ced–3 encodes a protein similar to mammalian interleukin–1β–converting enzyme" Cell (1993) 75:641–652.

Allison et al., "The yin and yang of T cell costimulation" *Science* (1995) 270:932–933.

Beidler et al., "The baculovirus p35 protein inhibits fas– and tumor necrosis factor–induced apoptosis" *J. Biol. Chem.* (1995) 270:16526–16528.

Blau et al., "Molecular medicine: Gene therapy—a novel form of drug delivery" *N. Eng. J. Med.* (1995) 333:1204–1207.

Boldin et al., "A novel protein that interacts with the death domain of Fas/APO1 contains a sequence motif related to the death domain" *J. Biol. Chem.* (1995) 270:7795–7798.

Boldin et al., "Self–association of the 'death domains' of the p55 tumor necrosis factor (TNF) receptor and Fas/APO1 prompts signaling for TNF and Fas/APO1 effects" *J. Biol. Chem.* (1995) 270:387–391.

Bose et al., "Ceramide synthase mediates daunorubicin–induced apoptosis: An alternative mechanism for generating death signals" *Cell* (1995) 82:405–414.

Boulakia et al., "Bcl–2 and adenovirus E1B 19 kDa protein prevent E1A–induced processing of CPP32 and cleavage of poly(ADP–ribose) polymerase" *Oncogene* (1996) 12:529–535.

Brunner et al., "Cell–autonomous Fas (CD95)/Fas–ligand interaction mediates activation–induced apoptosis in T–cell hybridomas" *Nature* (1995) 373:441–444.

Bump et al., "Inhibition of ICE family proteases by baculovirus antiapoptotic protein p35" *Science* (1995) 269:1885–1888.

Casciola–Rosen et al., "Specific cleavage of the 70–kDa protein component of the U1 small nuclear ribonucleoprotein is a characteristic biochemical feature of apoptotic cell death" *J. Biol. Chem.* (1994) 269:30757–30760.

Chinnaiyan et al., "FADD/MORT1 is a common mediator of CD95 (Fas/APO–1) and tumor necrosis factor receptor–induced apoptosis" *J. Biol. Chem.* (1996) 271:4961–4965.

Chinnaiyan et al., "Molecular ordering of the cell death pathway" *J. Biol. Chem.* (1996) 271:4573–4576.

Clem et al., "Prevention of apoptosis by a baculovirus gene during infection of insect cells" *Science* (1991) 254:1388–1390.

Clem et al., "Control of programmed cell death by the baculovirus genes p35 and iap" *Mol. & Cell. Biol.* (1994) 14:5212–5222.

Clement et al., "Fas and tumor necrosis factor receptor–mediated cell death: Similarities and distinctions" *J. Exp. Med.* (1994) 180:557–567.

Cleveland et al., "Contenders in FasL/TNF death signaling" *Cell* (1995) 81:479–482.

Cohen, "Apoptosis" *Immunology Today* (1993) 14:126–130.

Darmon et al., "Activation of the apoptotic protease CPP32 by cytotoxic T–cell–derived granzyme B" *Nature* (1995) 377:446–448.

Dhein et al., "Autocrine T–cell suicide mediated by APO–1/(Fas/CD95)" *Nature* (1995) 373:438–441.

Duan et al., "ICE–LAP3, a novel mammalian homologue of the *Caenorhabditis elegans* cell death protein CED–3 is activated during Fas– and tumor necrosis factor–induced apoptosis" *J. Biol. Chem.* (1996) 271:1621–1625.

Faucheu et al., "A novel human protease similar to the interleukin–1β converting enzyme induces apoptosis in transfected cells" *EMBO J.* (1995) 14:1914–1922.

Fernandes–Alnemri et al., "CPP32, a novel human apoptotic protein with homology to *Caenorhabditis elegans* cell death protein Ced–3 and mammalian interleukin–1β–converting enzyme" *J. Biol. Chem.* (1994) 269:30761–30764.

Fernandes–Alnemri et al., "Mch2, a new member of the apoptotic Ced–3/Ice cysteine protease gene family" *Cancer Res.* (1995) 55:2737–2742.

Fernandes–Alnemri et al., "Mch3, a novel human apoptotic cysteine protease highly related to CPP32" *Cancer Res.* (1995) 55:6045–6052.

Fisher et al., "Dominant interfering Fas gene mutations impair apoptosis in a human autoimmune lymphoproliferative syndrome" *Cell* (1995) 81:935–946.

Golstein et al., "Homology between reaper and the cell death domains of Fas and TNFR1" *Cell* (1995) 81:185–186.

Harper et al., "The p21 Cdk–interacting protein Cip1 is a potent inhibitor of G1 cyclin–dependent kinases" *Cell* (1993) 75:805–816.

Henderson et al., "Epstein–Barr virus–coded BHRF1 protein, a viral homologue of Bcl–2, protects human B cells from programmed cell death" *Proc. Natl. Acad. Sci. USA* (1993) 90:8479–8483.

Hengartner, "Life and death decisions: ced–9 and programmed cell death in *Caenorhabditis elegans*" *Science* (1995) 270:931.

Higuchi et al., "A general method of in vitro preparation and specific mutagenesis of DNA fragments: study of protein and DNA interactions" *Nucleic Acids Res.* (1988) 16:7361–7367.

Hsu et al., "The TNF receptor 1–associated protein TRADD signals cell death and NF–kB activation" *Cell* (1995) 81:495–504.

Hsu et al., "TRADD–TRAF2 and TRADD–FADD interactions define two distinct TNF receptor 1 signal transduction pathways" *Cell* (1996) 84:299–308.

Hu et al., "A novel RING finger protein interacts with the cytoplasmic domain of CD40" *J. Biol. Chem.* (1994) 269:30069–30072.

Hynes et al., "A target for tumour–directed therapy" *Nature Medicine* (1995) 1:631–632.

Kamens et al., "Identification and characterization of ICH–2, a novel member of the interleukin –1β–converting enzyme family of cysteine proteases" *J. Biol. Chem.* (1995) 270:15250–15256.

Kaufmann et al., "Specific proteolytic cleavage of poly(ADP–ribose) polymerase: An early marker of chemotherapy-–induced apoptosis" *Cancer Res.* (1993) 53:3976–3985.

Kischkel et al., "Cytotoxicity–dependent APO–1 (Fas/CD95)–associated proteins form a death–inducing signaling complex (DISC) with the receptor" *EMBO J.* (1995) 14:5579–5588.

Kuida et al., "Altered cytokine export and apoptosis in mice deficient in interleukin–1β converting enzyme" *Science* (1995) 267:2000–2003.

Lazebnik et al., "Cleavage of poly(ADP–ribose) polymerase by a proteinase with properties like ICE" *Nature* (1994) 371:346–347.

Li et al., "Mice deficient in IL–1β–converting enzyme are defective in production of mature IL–1β and resistant to endotoxic shock" *Cell* (1995) 80:401–411.

Liston et al., "Suppression of apoptosis in mammalian cells by NAIP and a related family of IAP genes" *Nature* (1996) 379:349–353.

Margolick et al., "Failure of T–cell homeostatis preceding AIDS in HIV–1 infection" *Nature Medicine* (1995) 1:674–680.

Martinou et al., "Viral proteins E1B19K and p35 protect sympathetic neurons from cell death induced by NGF deprivation" *J. Cell Biol.* (1995) 128:201–208.

McElvaney et al., "IL–6 release and airway administration of human CFTR cDNA adenovirus vector" *Nature Medicine* (1995) 1:182–184.

Milner, "DNA damage, p53 and anticancer therapies" *Nature Medicine* (1995) 1:879–880.

Miura et al., "Induction of apoptosis in fibroblasts by IL–1β–converting enzyme, a mammalian homolog of the *C. elegans* cell death gene ced–3" *Cell* (1993) 75:653–660.

Munday et al., "Molecular cloning and pro–apoptotic activity of $ECE_{rel}II$ and $ICE_{rel}III$, members of the ICE/CED–3 family of cysteine proteases" *J. Biol. Chem.* (1995) 270:15870–15876.

Na et al., "D4–GDI, a substrate of CPP32, is proteolyzed during Fas–induced apoptosis" *J. Biol. Chem.* (1996) 271:11209–11213.

Nicholson et al., "Identification and inhibition of the ICE/CED–3 protease necessary for mammalian apoptosis" *Nature* (1995) 376:37–43.

Nicholson, "ICE/CED3–like proteases as therapeutic targets for the control of inappropriate apoptosis" *Nature Biotechnol.* (1996) 14:297–301.

O'Rourke et al., "Thrombospondin 1 and thrombospondin 2 are expressed as both homo– and heterotimers" *J. Biol. Chem.* (1992) 267:24921–24924.

Oi et al., "Chimeric antibodies" *Bio/Techniques* (1986) 4:214–221.

Paigen, "A miracle enough: the power of mice" *Nature Medicine* (1995) 1:215–220.

Peter et al., "CD95 (APO–1/FAS)–associating signalling proteins" *Cell Death and Differentiation* (1996) 3:161–170.

Peters et al., "Ankyrins: Structure and function in normal cells and hereditary spherocytes" *Seminars in Hematol.* (1993) 30:85–118.

Rabizadeh et al., "Expression of the baculovirus p35 gene inhibits mammalian neural cell death" *J. Neurochem.* (1993) 61:2318–2321.

Roederer, "T–cell dynamics of immunodeficiency" *Nature Medicine* (1995) 1:621–622.

Ron et al., "pGSTag—a versatile bacterial expression plasmid for enzymatic labeling of recombinant proteins" *Bio/Techniques* (1992) 13:866–869.

Rothe et al., "TRAF2–mediated activation of NF–kB by TNF receptor 2 and CD40" *Science* (1995) 269:1424–1427.

Rothe et al., "The TNFR2–TRAF signaling complex contains two novel proteins related by baculoviral inhibitor of apoptosis proteins" *Cell* (1995) 83:1243–1252.

Roy et al., "The gene for neuronal apoptosis inhibitory protein is partially deleted in individuals with spinal muscular atrophy"*Cell* (1995) 80:167–178.

Schlegel et al., "CPP32/apopain is a key interleukin 1β converting enzyme–like protease involved in Fas–mediated apoptosis" *J. Biol. Chem.* (1996) 271:1841–1844.

Song, "Aggregation of the intracellular domain of the Type 1 tumor necrosis factor receptor defined by the two–hybrid system" *J. Biol. Chem.* (1994) 269:22492–22495.

Spira et al., "The identification of monoclonal class switch variants by sib selection and an ELISA assay" *J. Immunol. Meth.* (1984) 74:307–315.

Stanger et al., "RIP: A novel protein containing a death domain that interacts with Fas/APO–1 (CD95) in yeast and causes cell death" *Cell* (1995) 81:513–523.

Steplewski et al., "Isolation and characterization of anti–monosialoganglioside monoclonal antibody 19–9 class–switch variants" *Proc. Natl. Acad. Sci. USA* (1985) 82:8653–8657.

Stinchcomb, "Constraining the cell cycle: Regulating cell division and differentiation by gene therapy" *Nature Medicine* (1995) 1:1004–1006.

Studier, "Use of bacteriophage T7 lysozyme to improve an inducible T7 expression system" *J. Mol. Biol.* (1991) 219:37–44.

Sugimoto et al., "Baculovirus p35 prevents developmentally programmed cell death and rescues a ced–9 mutant in the nematode *Caenorhabditis elegans*" *EMBO J.* (1994) 13:2023–2028.

Tamura et al., "An IRF–1–dependent pathway of DNA damage–induced apoptosis in mitogen–activated T lymphocytes" *Nature* (1995) 376:596–599.

Tanaka et al., "Fas ligand in human serum" *Nature Medicine* (1996) 2:317–322.

Tartaglia et al., "Two TNF receptors" *Immunol. Today* (1992) 13:151–153.

Tartaglia et al., "A novel domain within the 55 kd TNF receptor signals cell death" *Cell* (1993) 74:845–853.

Tewari et al., "Fas– and tumor necrosis factor–induced apoptosis is inhibited by the poxvirus crmA gene product" *J. Biol. Chem.* (1995) 270:3255–3260.

Tewari et al., "CrmA–inhibitable cleavage of the 70–kDa protein component of the U1 small nuclear ribonucleoprotein during Fas– and tumor necrosis factor–induced apoptosis" *J. Biol. Chem.* (1995) 270:18738–18741.

Tewari et al., "Yama/CPP32β, a mammalian homolog of CED–3, is a CrmA–inhibitable protease that cleaves the death substrate poly(ADP–ribose) polymerase" *Cell* (1995) 81:801–809.

vanBockxmeer et al., "Premature ischaemic heart disease and the gene for coagulation factor V" *Nature Medicine* (1995) 1:185.

Verheij et al., "Requirement for ceramide–initiated SAPK/JNK signalling in stress–induced apoptosis" *Nature* (1996) 380:75–79.

Vermes et al., "Apoptosis and programmed cell death in health and disease" (1994) Academic Press, Inc., pp. 177–247.

Vito et al., Interfering witih apoptosis: $Ca^{2+}$–binding protein ALG–2 and Alzheimer's disease gene ALG–3 *Science* (1996) 271:521–525.

Wang et al., "Ich–1, an Ice/ced–3–related gene, encodes both positive and negative regulators of programmed cell death" *Cell* (1994) 78:739–750.

Wang et al., "Cleavage of sterol regulatory element binding proteins (SREBPs) by CPP32 during apoptosis" *EMBO J.* (1996) 15:1012–1020.

Watanabe–Fukunaga et al., "Lymphoproliferation disorder in mice explained by defects in Fas antigen that mediates apoptosis" *Nature* (1992) 356:314–317.

Westendorp et al., "Sensitization of T cells to CD95–mediated apoptosis by HIV–1 Tat and gp120" *Nature* (1995) 375:497–503.

Whyte et al., "The last cut is the deepest" *Nature* (1995) 376:17–18.

Williams et al., "Apoptotic cell death induced by intracellular proteolysis" *J. Immunol.* (1994) pp. 4247–4255.

Woo, "Apoptosis and loss of renal tissue in polycystic kidney diseases" *N. Eng. J. Med.* (1995) 333:18–25.

Wu et al., "Interaction of the erythropoietin and stem-cell-factor receptors" *Nature* (1995) 377:242–246.

Xue et al., "Inhibition of the *Caenorhabditis elegans* cell-death protease CED–3 by a CED–3 cleavage site in baculovirus p35 protein" *Nature* (1995) 377:248–251.

Yuan et al., "The *C. elegans* cell death gene ced–3 encodes a protein similar to mammalian interleukin–1β–converting enzyme" *Cell* (1993) 75:641–652.

Zheng et al., "Induction of apoptosis in mature T cells by tumour necrosis factor" *Nature* (1995) 377:348–351.

Chinnaiyan et al. "Signal Transduction by DR3, a Death Domain–Containing Receptor Related to TNFR–1 and CD95" *Science* (1996) 274:990–992.

Hu et al. "A Novel Family of Viral Death Effector Domain–containing Molecules that Inhibit Both CD–95– and Tumor Necrosis Factor Receptor–1–induced Apoptosis" *J. Biol. Chem.* (1997) 272:9621–9624.

Pan et al. "The Receptor for the Cytotoxic Ligand TRAIL" *Science* (1997) 276:111–113.

Rathmell et al. "Expansion or Elimination of B Cells In Vivo: Dual Roles for CD40– and Fas (CD95)–Ligands Modulated by the B Cell Antigen Receptor" *Cell* (1996) 87:319–329.

Strand et al. "Lymphocyte apoptosis induced by CD95 (APO–1/Fas) ligand–expressing tumor cells—A mechanism of immune evasion?" *Nature Medicine* (1996) 2(12):1361–1366.

Tewari et al. "CrmA, a poxvirus–encoded serpin, inhibits cytotoxic T–lymphocyte–mediated apoptosis" *J. Biol. Chem.* (1995) 270(39):22705–22708.

Baglioni "Mechanisms of cytotoxicity, cytolysis, and growth stimulation by TNF" *Tumor Necrosis Factors. The Molecules and Their Emerging Role in Medicine* (1992) B. Beutler, M.D., etd., Raven Press, New York. A title page and table of contents are enclosed herewith.

Chinnaiyan et al., "FADD, a novel death domain–containing protein, interacts with the death domain of Fas and initiates apoptosis" *Cell* (1995) 81:505–512.

Herlyn et al., "Anti–idiotypic antibodies bear the internal image of a human tumor antigen" *Science* (1986) 232:100–102.

Maekawa et al. "Molecular cloning of a novel protein–tyrosine phosphatase containing a membrane–binding domain and GLGF repeats" *FEBS Letters* 337 (1994) 200–206.

Morrison, et al. "Direct Activation of the Serine/Threonine Kinase Activity of Raf–1 through Tyrosine Phosphorylation by the PDGF β–Receptor" *Cell* (1989) 58:649–57.

Kuby, "Immunology" W.H. Freeman and Company, N.Y. (1992) 257.

Smith et al. "CrmA expression in T lymphocytes of transgenic mice inhibits CD95 (Fas/APO–1)–transduced apoptosis, but does not cause lymphadenopathy or autoimmune disease" *The EMBO Journal* (1996) 15:5167–5176.

EMBL Database, Accession No. PIR P91375 Kotwal JG, Moss B. (Jan. 12, 1990) and US–A–7285510 (Jun. 20, 1989) XP002013939, 2 pages total.

EMBL Database, Accession No. T10341, Sequence reference HS341, M.B. Soares et al., (Apr. 17, 1994) XP002013935, 1 page total.

Marshall et al. "Sequence and Functional Expression of a single α subunit of an insect nicotinic acetylcholine receptor" *The EMBO Jrnl.* 9(13):4391–98 (1990).

Gagliardini, et al *Science* 1994, vol. 263 pp. 826–828.

Soares, M.B. GenBank Accession No. T10341. Jun. 7, 1994.

Orkin, et al. "Report and Recommendations of the Panel to Assess the NIH investment in Research on Gene Therapy" (Dec. 7, 1995).

Baglioni "Mechanisms of cytotoxicity, cytolysis, and growth stimulation by TNF" *Tumor Necrosis Factors. The Molecules and Their Emerging Role in Medicine* (1992) B. Beutler, M.D., etd., Raven Press, New York. A title page and table of contents are enclosed herewith.

Chinnaiyan et al., "FADD, a novel death domain–containing protein, interacts with the death domain of Fas and initiates apoptosis" *Cell* (1995) 81:505–512.

Herlyn et al., "Anti–idiotypic antibodies bear the internal image of a human tumor antigen" *Science* (1986) 232:100–102.

Maekawa et al. "Molecular cloning of a novel protein–tyrosine phosphatase containing a membrane–binding domain and GLGF repeats" *FEB Letters* 337 (1994) 200–206.

Morrison, et al., "Direct Activation of the Serine/Threonine Kinase Activity of Raf–1 through Tyrosine Phosphorylation by the PDGF β–Receptor" *Cell* (1989) 58:649–57.

Daniel, C., et al., "Mapping of Linear Antigenic Sites on the S Glycoprotein of a Neurotropic Murine Coronavirus With Synthetic Peptides: A Combination of Nine Prediction Algorithms Fails to Identify Relevant Epitopes and Peptide Immunogenicity is Drastically Influenced by the Nature of the Protein Carrier," *Virology* –202:540–549 (1994).

Moss, B., "Poxviridae and Their Replication," *Virology*–2$^{nd}$ ed., Fields., B.N., et al., eds., Raven Press, New York Chapter 74, pp. 2079–2111 (1990).

Owen–Schaub, L.B., et al., "Anti–Fas on Nonhematopoietic Tumors: Levels of Fas/APO–1 and bcl–2 are not Predictive of Biological Responsiveness," *Cancer Research*–54:1580–1586 (1994).

Sambrook et al., "Chapter 17 Expression of Cloned Genes in Escherichia Coli," *Molecular Cloning: A Laboratory Manual*, 2$^{nd}$ Eds., Vols. 1,2 and 3, Cold Harbor Laboratory Press, Cold Spring Harbor, NY (1989).

Sambrook et al. molecular cloning a Laboratory Manual Cold Spring Habor: Laboratory press. 1989 pages 11.2–11.3.*

* cited by examiner

```
GGCACGAGCGGATGGGTGCTATTGTGAGGCGGTTGTAGAAGAGTTTCGTGAGTGCTCGCAGCTCATACCT
GTGGCTGTGTATCCGTGGCCACAGCTGGTTGGCGTCGCCTTGAAATCCCAGGCCGTGAGGAGTTAGCGAG
CCCTGCTCACACTCGGCGCTCTGGTTTTCGGTGGGTGTGCCCTGCACCTGCCTCTTCCCGCATTCTCATT
AATAAAGGTATCCATGGAGAACACTGAAAACTCAGTGGATTCAAAATCCATTAAAAATTTGGAACCAAAG
ATCATACATGGAAGCGAATCAATGGACTCTGGAATATCCCTGGACAACAGTTATAAAATGGATTATCCTG
AGATGGGTTTATGTATAATAATTAATAATAAGAATTTTCATAAAAGCACTGGAATGACATCTCGGTCTGG
TACAGATGTCGATGCAGCAAACCTCAGGGAAACATTCAGAAACTTGAAATATGAAGTCAGGAATAAAAAT
GATCTTACACGTGAAGAAATTGTGGAATTGATGCGTGATGTTTCTAAAGAAGATCACAGCAAAAGGAGCA
GTTTTGTTTGTGTGCTTCTGAGCCATGGTGAAGAAGGAATAATTTTTGGAACAAATGGACCTGTTGACCT
GAAAAAAATAACAAACTTTTTCAGAGGGGATCGTTGTAGAAGTCTAACTGGAAAACCCAAACTTTTCATT
ATTCAGGCCTGCCGTGGTACAGAACTGGACTGTGGCATTGAGACAGACAGTGGTGTTGATGATGACATGG
CGTGTCATAAAATACCAGTGGAGGCCGACTTCTTGTATGCATACTCCACAGCACCTGGTTATTATTCTTG
GCGAAATTCAAAGGATGGCTCCTGGTTCATCCAGTCGCTTTGTGCCATGCTGAAACAGTATGCCGACAAG
CTTGAATTTATGCACATTCTTACCCGGGTTAACCGAAAGGTGGCAACAGAATTTGAGTCCTTTTCCTTTG
ACGCTACTTTTCATGCAAAGAAACAGATTCCATGTATTGTTTCCATGCTCACAAAAGAACTCTATTTTTA
TCACTAAAGAAATGGTTGGTTGGTGGTTTTTTTTAGTTTGTATGCCAAGTGAGAAGATGGTATATTTGGT
ACTGTATTTCCCTCTCATTTGGGCCTACTCTCATGCTG
```

FIG. 1A

```
MENTENSVDSKSIKNLEPKIIHGSESMDSGISLDNSYKMDYPEMGLCIIINNKNFHKSTGMTSRSGTDVD
AANLRETFRNLKYEVRNKNDLTREEIVELMRDVSKEDHSKRSSFVCVLLSHGEEGIIFGTNGPVDLKKIT
NFFRGDRCRSLTGKPKLFIIQACRGTELDCGIETDSGVDDDMACHKIPVEADFLYAYSTAPGYYSWRNSK
DGSWFIQSLCAMLKQYADKLEFMHILTRVNRKVATEFESFSFDATFHAKKQIPCIVSMLTKELYFYH
```

FIG. 1B

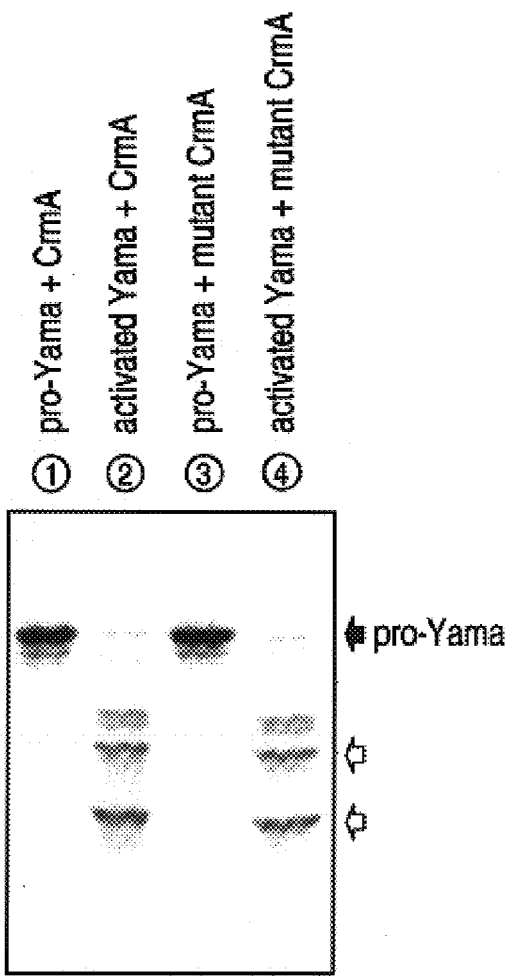
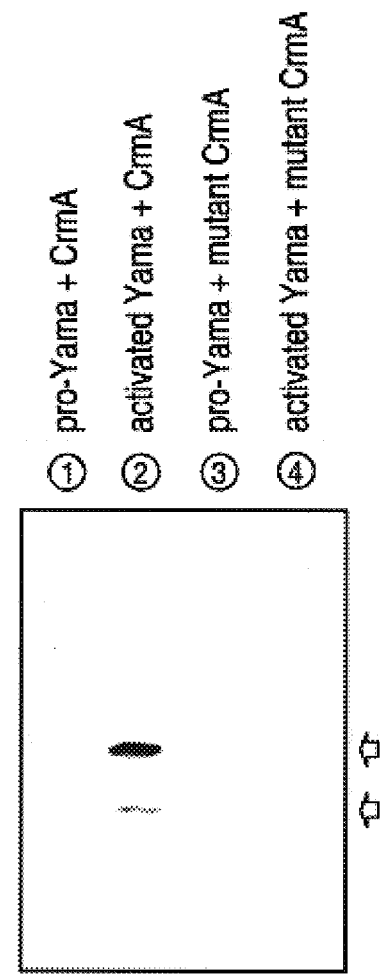
FIG. 5A  FIG. 5B

```
        10        20        30        40        50        60
TCCATGGAAGAACGAAAGTAGTATAAAAGTAATAAAACAAAAAAAAGAATATAAAAAATT 70        80        90       100       110       120
TATAGCCACTTTCTTTGAGGACTGTTTTCCTGAAGGAAATGAACCTCTGGAATTAGTTAG 130       140       150       160       170       180
ATATATAGAATTAGTATACACGCTAGATTATTCTCAAACTCCTAATTATGACAGACTACG 190       200       210       220       230       240
TAGACTGTTTATACAAGATTGAAAATATATTTCTTTTTATTGAGTGGTGGTAGTTACGGA 250       260       270       280       290       300
TATCTAATATTAATATTAGACTATCTCTATCGTCACACAACAAAATCGATTGCCATGGAT
                                                          M  D 310       320       330       340       350       360
ATCTTCAGGGAAATCGCATCTTCTATGAAAGGAGAGAATGTATTCATTTCTCCACCGTCA
 I  F  R  E  I  A  S  S  M  K  G  E  N  V  F  I  S  P  P  S 370       380       390       400       410       420
ATCTCGTCAGTATTGACAATACTGTATTATGGAGCTAATGGATCCACTGCTGAACAGCTA
 I  S  S  V  L  T  I  L  Y  Y  G  A  N  G  S  T  A  E  Q  L 430       440       450       460       470       480
TCAAAATATGTAGAAAAGGAGGCGGACAAGAATAAGGATGATATCTCATTCAAGTCCATG
 S  K  Y  V  E  K  E  A  D  K  N  K  D  D  I  S  F  K  S  M 490       500       510       520       530       540
AATAAAGTATATGGGCGATATTCTGCAGTGTTTAAAGATTCCTTTTTGAGAAAAATTGGA
 N  K  V  Y  G  R  Y  S  A  V  F  K  D  S  F  L  R  K  I  G 550       560       570       580       590       600
GATAATTTCCAAACTGTTGACTTCACTGATTGTCGCACTGTAGATGCGATCAACAAGTGT
 D  N  F  Q  T  V  D  F  T  D  C  R  T  V  D  A  I  N  K  C 610       620       630       640       650       660
GTTGATATCTTCACTGAGGGGAAAATTAATCCACTATTGGATGAACCATTGTCTCCAGAT
 V  D  I  F  T  E  G  K  I  N  P  L  L  D  E  P  L  S  P  D 670       680       690       700       710       720
ACCTGTCTCCTAGCAATTAGTGCCGTATACTTTAAAGCAAAATGGTTGATGCCATTTGAA
 T  C  L  L  A  I  S  A  V  Y  F  K  A  K  W  L  M  P  F  E
```

FIG. 8A

```
              730       740       750       760       770       780
         AAGGAATTTACCAGTGATTATCCCTTTTACGTATCTCCAACGGAAATGGTAGATGTAAGT
          K  E  F  T  S  D  Y  P  F  Y  V  S  P  T  E  M  V  D  V  S 790       800       810       820       830       840
         ATGATGTCTATGTACGGCGAGGCATTTAATCACGCATCTGTAAAAGAATCATTCGGCAAC
          M  M  S  M  Y  G  E  A  F  N  H  A  S  V  K  E  S  F  G  N 850       860       870       880       890       900
         TTTTCAATCATAGAACTGCCATATGTTGGAGATACTAGTATGGTGGTAATTCTTCCAGAC
          F  S  I  I  E  L  P  Y  V  G  D  T  S  M  V  V  I  L  P  D 910       920       930       940       950       960
         AATATTGATGGACTAGAATCCATAGAACAAAATCTAACAGATACAAATTTTAAGAAATGG
          N  I  D  G  L  E  S  I  E  Q  N  L  T  D  T  N  F  K  K  W 970       980       990      1000      1010      1020
         TGTGACTCTATGGATGCTATGTTTATCGATGTGCACATTCCCAAGTTTAAGGTAACAGGC
          C  D  S  M  D  A  M  F  I  D  V  H  I  P  K  F  K  V  T  G 1030      1040      1050      1060      1070      1080
         TCGTATAATCTGGTGGATGCGCTAGTAAAGTTGGGACTGACAGAGGTGTTCGGTTCAACT
          S  Y  N  L  V  D  A  L  V  K  L  G  L  T  E  V  F  G  S  T 1090      1100      1110      1120      1130      1140
         GGAGATTATAGCAATATGTGTAATTCAGATGTGAGTGTCGACGCTATGATCCACAAAACG
          G  D  Y  S  N  M  C  N  S  D  V  S  V  D  A  M  I  H  K  T 1150      1160      1170      1180      1190      1200
         TATATAGATGTCAATGAAGAGTATACAGAAGCAGCTGCAGCAACTTGTGCGCTGTTGGCA
          Y  I  D  V  N  E  E  Y  T  E  A  A  A  A  T  C  A  L  V  A 1210      1220      1230      1240      1250      1260
         GACTGTGCATCAACAGTTACAAATGAGTTCTGTGCAGATCATCCGTTCATCTATGTGATT
          D  C  A  S  T  V  T  N  E  F  C  A  D  H  P  F  I  Y  V  I 1270      1280      1290      1300      1310      1320
         AGGCATGTCGATGGCAAAATTCTTTTCGTTGGTAGATATTGCTCTCCAACAACTAATTAA
          R  H  V  D  G  K  I  L  F  V  G  R  Y  C  S  P  T  T  N  *

1330      1340      1350      1360      1370      1380
         ATCACATTCTTAATATTAGAATATTAGAATATTATATAGTTAAGATTTTTACTAATTGGT
```

FIG. 8B

```
       1390      1400      1410      1420      1430      1440
TAACCATTTTTTTAAAAAAATAGAAAAAAAACATGTTATATTAGCGAGGGTCGTTATTCT 1450      1460
TCCAATTGCAATTGGTAAGATGACGGCC
```

FIG. 8C

METHOD AND COMPOSITION FOR REGULATING APOPTOSIS

This application is a continuation-in-part of U.S. Ser. No. 08/389,812, filed Feb. 13, 1995, the contents of which are hereby incorporated by reference into the present disclosure.

This invention was made in part with support from the United States government under Grant No. CA64803 from the National Institutes of Health. Accordingly, the United States government has rights in this invention.

TECHNICAL FIELD

This invention relates to a protease that is an effector component of a mammalian cell death pathway. More specifically, it relates to nucleic acid molecules encoding the protease and methods of use of the protease and nucleic acids encoding the protease.

BACKGROUND OF THE INVENTION

Apoptosis, or programmed cell death (PCD), is of fundamental importance to biological processes including embryogenesis, normal cellular development of multicellular organisms and the development of the immune system (Ellis et al. (1991) *Ann. Rev. Cell Biol.* 7:663–698). It is a type of cell death that is fundamentally distinct from degenerative death or necrosis in that it is an active process of gene-directed cellular self-destruction which in some instances, serves a biologically meaningful homeostatic function. This can be contrasted to necrosis which is cell death occurring as the result of severe injurious changes in the environment of infected cells. For a general review of apoptosis, see Tomei, L. D. and Cope, F. O. *Apoptosis: The Molecular Basis of Cell Death* (1991) Cold Spring Harbor Press, N.Y.; Tomei, L. D. and Cope, F. O. *Apoptosis II: The Molecular Basis of Apoptosis in Disease* (1994) Cold Spring Harbor Press, N.Y.; and Duvall and Wyllie (1986) *Immun. Today* 7(4):115–119.

Morphologically, apoptosis is characterized by the rapid condensation of the cell with preservation of membranes. Synchronistically with the compaction of chromatin, several biochemical changes occur in the cell. Nuclear DNA is cleaved at the linker regions between nucleosomes to produce fragments which are easily demonstrated by agarose gel electrophoresis wherein a characteristic ladder develops.

Apoptosis has been linked to many biological processes, including embryogenesis, development of the immune system, elimination of virus-infected cells, and the maintenance of tissue homeostasis. Apoptosis also occurs as a result of human immunodeficiency virus (HIV) infection of CD4+ T lymphocytes (T cells). Indeed, one of the major characteristics of AIDS is the gradual depletion of CD4+ T lymphocytes during the development of the disease. Several mechanisms, including apoptosis, have been suggested to be responsible for the CD4 depletion.

The depletion of CD4+ T cells results in the impairment of the cellular immune response. It has been proposed that an inappropriate activation-induced T cell PCD causes the functional and numerical abnormalities of $T_H$ cells from HIV-infected patients, that leads to the near collapse of the patient's immune system.

This invention has identified an effector component of mammalian apoptosis which is an element of the apoptotic cell death pathway. Accordingly, this invention provides compositions and methods to modulate apoptotic cell death and associated biological processes.

SUMMARY OF THE INVENTION

This invention provides non-naturally occurring and isolated naturally occurring nucleic acid molecules which encode proteins designated Yama Pro-Yama.

This invention also provides a recombinant polynucleotide having a polynucleotide sequence as shown in FIG. 1. Further provided by this invention are fragments of the above-identified nucleic acid molecules. Specific examples of these fragments are nucleic acid molecules coding for the polypeptides designated herein p20 Yama and p11 Yama.

Also provided by this invention is a recombinant nucleic acid molecule encoding a polypeptide having the amino acid sequence depicted in FIG. 1 or a fragment of this amino acid sequence. Further provided by this invention is a non-naturally occurring nucleic acid molecule encoding mutant CrmA protein and a dominant inhibitory Yama. Vectors and host cells containing these nucleic acid molecules are further provided.

Purified and recombinantly produced proteins and polypeptides designated Yama Pro-Yama, p20 Yama, p11 Yama, mutant CrmA and mutant Yama also are provided herein.

Methods of modulating a cellular function regulated by the Fas receptor pathway in a cell is provided herein. The methods comprise introducing into the cell a Yama nucleic acid molecule. These methods can be practiced in vitro, in vivo and ex vivo.

This invention provides compositions and methods for preventing or inhibiting apoptosis in a suitable cell by introducing into the cell a nucleic acid molecule coding for a gene product having CrmA biological activity such as dominant inhibitory Yama or alternatively, the crmA gene product.

Also provided by this invention are compositions and methods for preventing or inhibiting induced apoptosis in a suitable cell by introducing into the cell a nucleic acid molecule coding for a gene product having CrmA biological activity or the gene product so that induced apoptosis is prevented or inhibited.

Further provided by this invention are compositions and methods for maintaining T cell viability in a subject infected with or susceptible to infection with the human immunodeficiency virus by administering to the subject an effective amount of a nucleic acid molecule coding for a gene product having CrmA biological activity or the CrmA gene product.

BRIEF DESCRIPTION OF THE FIGURES

FIGS. 1A and 1B (SEQ ID NO:5 and SEQ ID NO:6) shows the open reading frame and deduced amino acid sequence of the protein designated herein as Pro-Yama. In the nucleotide sequence shown in FIG. 1A, the initiator methionine begins at nucleotide 224.

Figure 2A:
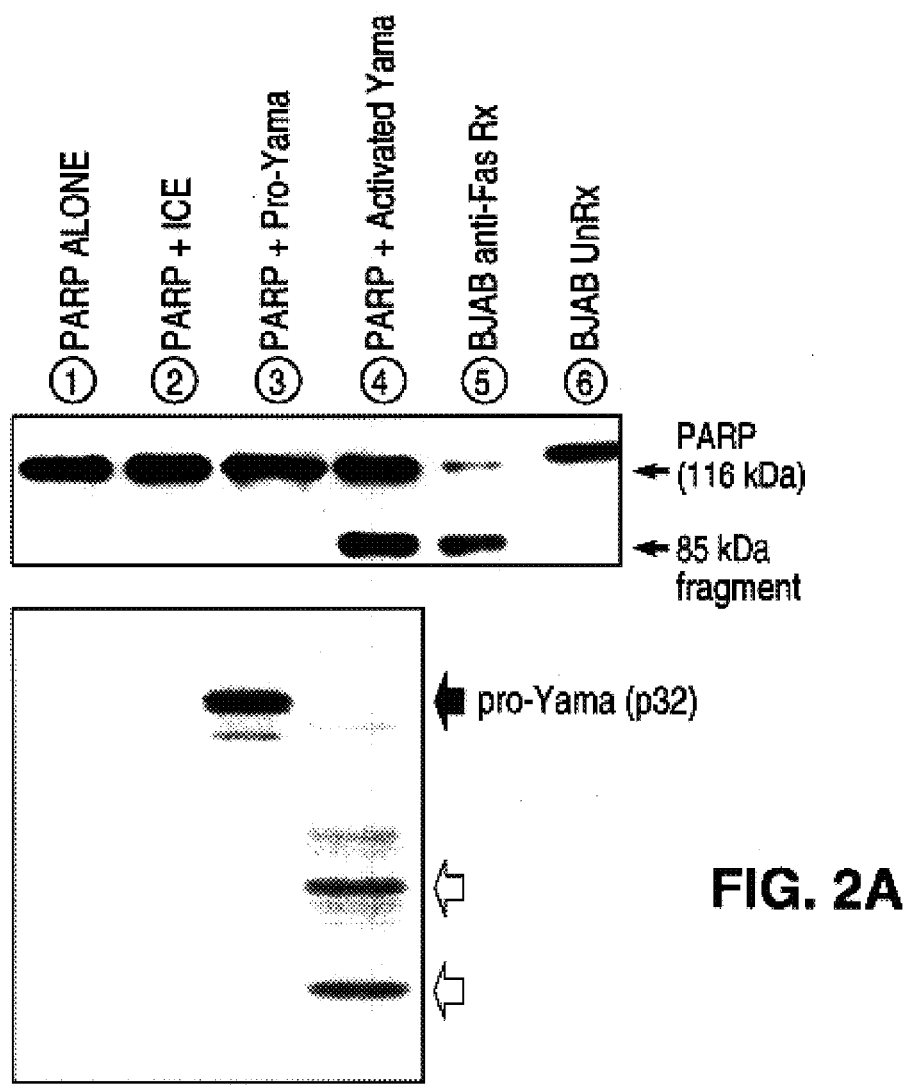
FIGS. 2A and 2B show that PRO-YAMA is a protease zymogen that, upon activation, cleaves PARP in vitro to the 85 kDa apoptotic fragment.

In the top panel of FIG. 2A it is shown that 6xHis-tagged Yama was expressed and labeled using [$^{35}$S]-Met in an in vitro transcription/translation reaction and purified by affinity chromatography on sequential DEAE-sepharose and nickel chelate columns as described in the experimental section below. In vitro reactions were assembled in which 0.586 µg purified PARP was incubated for 2 hours at 37° C. with either buffer only (Lane 1), ICE (Lane 2), purified PRO-YAMA (Lane 3), or purified PRO-YAMA after activation with ICE (Lane 4). Following incubation, one fifth of each reaction was analyzed by SDS-PAGE and immunoblotting using monoclonal antibody C-2-10 directed against PARP. Whole cell lysates from BJAB cells undergoing anti-Fas-induced apoptosis (Lane 5) or from untreated BJAB cells (Lane 6) were run alongside the in vitro reaction samples. Shown in the bottom panel are the results when equal quantities of the in vitro reactions represented in Lanes 1–4 of FIG. 2A were resolved by SDS-PAGE and the dried gel was subjected to Phosphorimager analysis to assess the state of the radio-labeled Yama protein. The filed-in arrow indicates the migration of purified PRO-YAMA, which is designated as the full-length p32 form. The open arrows indicate the two major proteolytic fragments observed after activation of PRO-YAMA by ICE, and are presumed to correspond to the putative p20 and p11 subunits predicted from cleavage at Asp residues in PRO-YAMA.

Figure 2B:
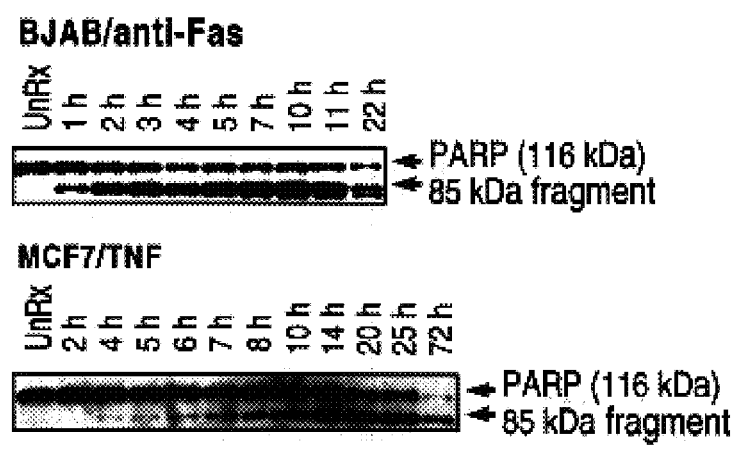

FIG. 2B shows that cleavage of PARP to an 85 kDa fragment is a characteristic feature of both Fas- and TNF-induced apoptosis. In the top panel, BJAB cells were either left untreated (UnRx) or treated with agonist anti-Fas antibody (250 ng/ml) for the indicated time periods and cell lysates prepared and analyzed by immunoblotting using anti-PARP monoclonal antibody C-2-10 as described in the experimental section below. In the bottom panel, MCF7 cells were either left untreated (UnRx) or treated with recombinant TNF (40 ng/ml) for the indicated time periods. Cell lysates were similarly analyzed.

Figure 3A:
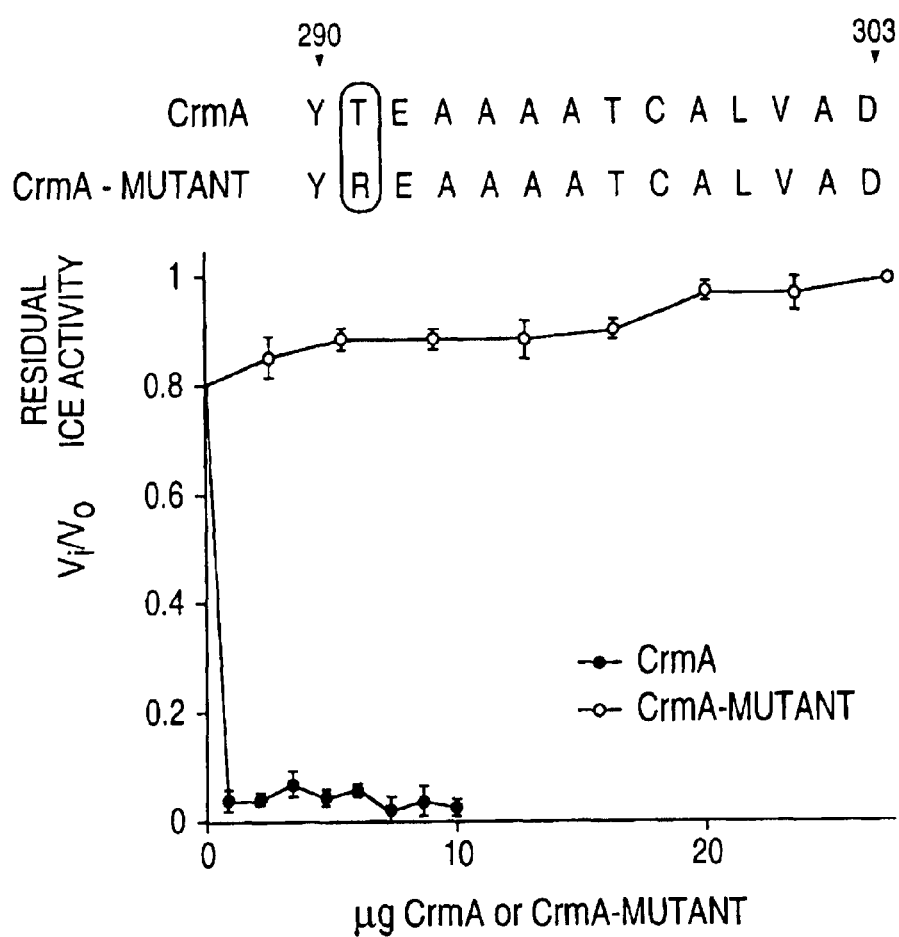
Figure 3B:
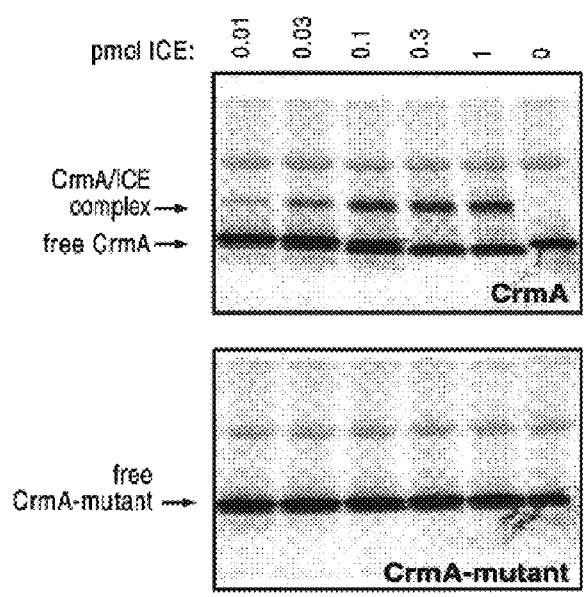
Figure 3C:
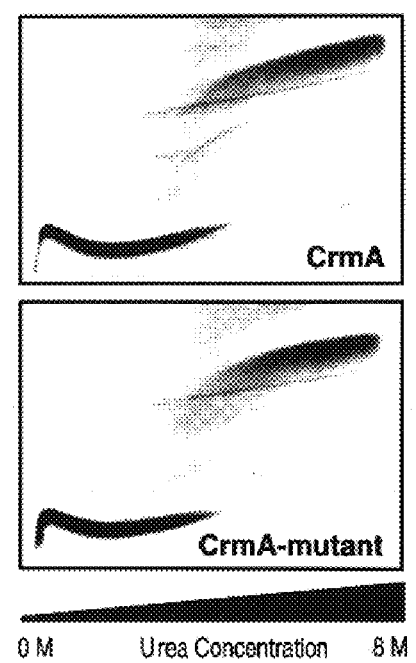

FIGS. 3A through 3C show that a point mutation in the reactive site loop (RSL) of CrmA inactivates its ability to inhibit ICE.

In FIG. 3A (top)(SEG ID NO:7 and SEQ ID NO:8), the reactive site loop sequences of CrmA and CrmA-mutant are compared. Amino acid 291 of wild-type CrmA, was altered from Thr to Arg by site-directed mutagenesis. The bottom panel shows protein expression in E. coli as 6xHis fusions and purification as described in the experimental section below. Briefly, 44 ng aliquots of ICE were titrated with the indicated amounts of purified CrmA (open squares) or CrmA-mutant (filled circles) protein. Residual ICE activity, expressed as the ratio of the inhibited rate ($v_i$) to the uninhibited rate ($v_o$), was determined with a chromogenic ICE substrate and plotted against the quantity of CrmA. ICE activity was abolished by as little as 300 ng of CrmA, whereas no inhibition was detected with CrmA-mutant protein, even using 30 µg, representing a 500-fold molar excess over the enzyme.

FIG. 3B shows that a CrmA-mutant does not form a complex with ICE. [$^{35}$S]-Met-labeled CrmA or CrmA-mutant proteins were produced by coupled transcription/translation of their respective genes. The indicated amounts of ICE were added directly to the diluted lysates and incubated as described in the experimental section below, following which samples were resolved by non-denaturing PAGE and the radioactive signals detected using a Phosphorimager. Mutant CrmA failed to form a complex with ICE; indeed, ICE appeared to have no effect on this protein. In comparison, part of the wild-type CrmA formed a complex whereas the rest was cleaved in a manner that typifies the interaction of ICE with CrmA (see Komiyama et al. (1994) J. Biol. Chem. 269:19331–19337).

FIG. 3C shows that the tertiary structures of CrmA and CrmA-mutant proteins are indistinguishable as assessed by transverse urea gradient polyacrylamide gel electrophoresis (TUG-PAGE). [$^{35}$S]-Met-labeled CrmA or CrmA-mutant proteins were generated by coupled transcription/translation and analyzed by TUG-PAGE as described in the experimental section below. The gels were dried and analyzed using a Phosphorimager to detect each protein's unfolding signature. No difference in the signatures was observed, indicating that the point mutation in CrmA-mutant did not disrupt the protein's tertiary structure.

Figure 4A:
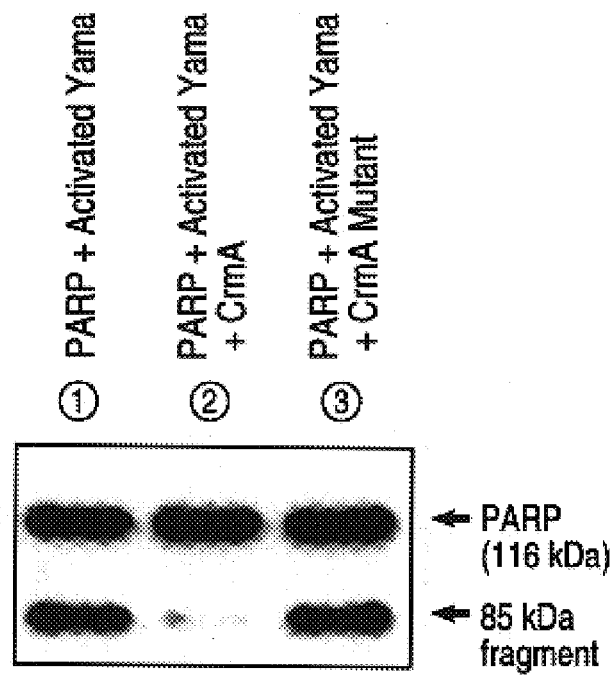
Figure 4B:
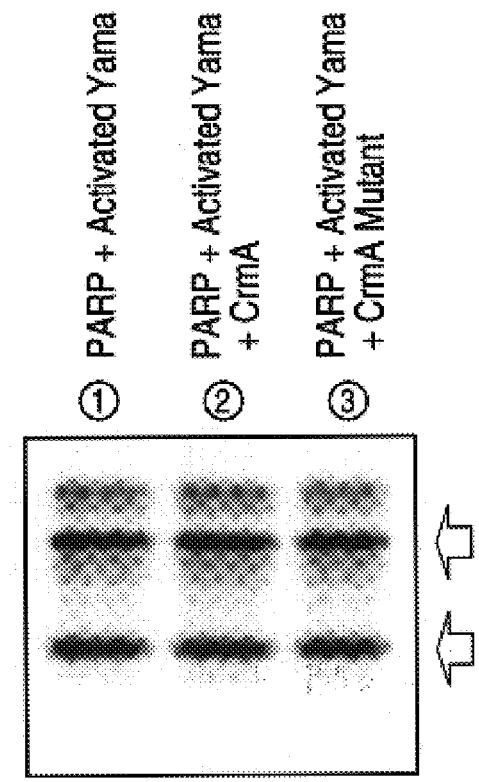

FIGS. 4A and 4B shows cleavage of PARP by activated Yama in vitro is inhibitable by CrmA but not by an equivalent amount of CrmA-mutant. Shown in the top panel are the results of [$^{35}$S] -Met-labeled Yama that was generated, purified and activated by ICE as described in the experimental section below. Purified, activated Yama was then incubated for 2 hours at 37° C. with 0.586 µg purified PARP in the presence of either buffer (Lane 1), 270 pmol CrmA (Lane 2) or 270 pmol CrmA-mutant (Lane 3) proteins as described below. Following the incubation with PARP, one-fifth of each reaction was analyzed by immunoblotting using anti-PARP monoclonal antibody C-2-10. In FIG. 4B, equivalent amounts of each of the above reactions were subjected to SDS-PAGE and the dried gel analyzed using a Phosphorimager to assess the state of the labeled Yama protein. The open arrows indicated the position of the two major products observed in preparations of activated Yama, and are presumed to correspond to the putative p20 and p11 subunits predicted from the amino acid sequence of Yama.

FIGS. 5A and 5B show that CrmA directly interacts with activated Yama but not with PRO-YAMA.

FIG. 5A is a Phosphorimager scan of reaction samples prior to immunoprecipitation analysis. Eighty (80) µl reactions were assembled in which either radiolabeled pro-Yama (Lanes 1 and 3) or radiolabeled activated Yama (Lanes 2 and 4) were mixed with either 358 pmol CrmA (Lanes 1 and 2) or 358 pmol CrmA-mutant (Lanes 3 and 4) recombinant proteins. Ten (10) µl of each reaction was resolved by SDS-PAGE and PRO-YAMA or activated Yama were detected by phosphorimaging analysis. The filled-in arrow indicates the migration of PRO-YAMA (p32), whereas the open arrows indicate the putative p20 and p11 subunits of activated Yama.

FIG. 5B is an immunoprecipitation of reaction samples with a polyclonal CrmA antiserum. Thirty-five (35) µl of each of the above reactions was subjected to immunoprecipitation using a rabbit polyclonal CrmA antiserum as described below. Precipitates were resolved by SDS-PAGE and radiolabeled proteins detected using a Phosphorimager. The open arrows indicate the putative p20 and p11 subunits of activated Yama.

Figure 6A:
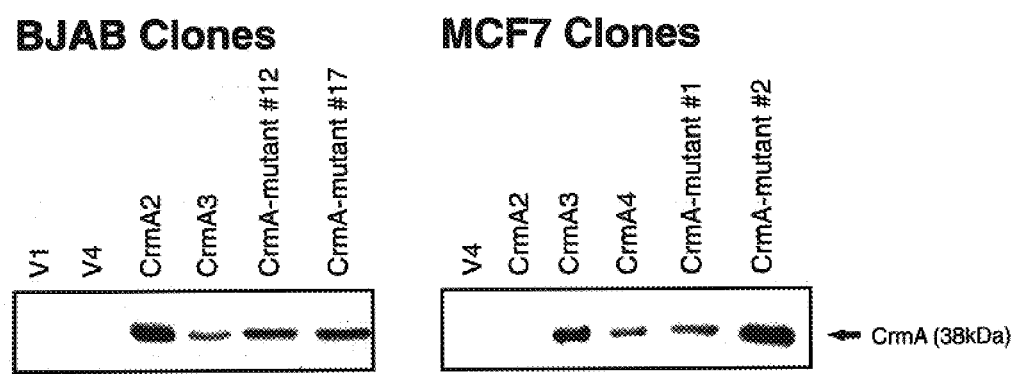
Figure 6B:
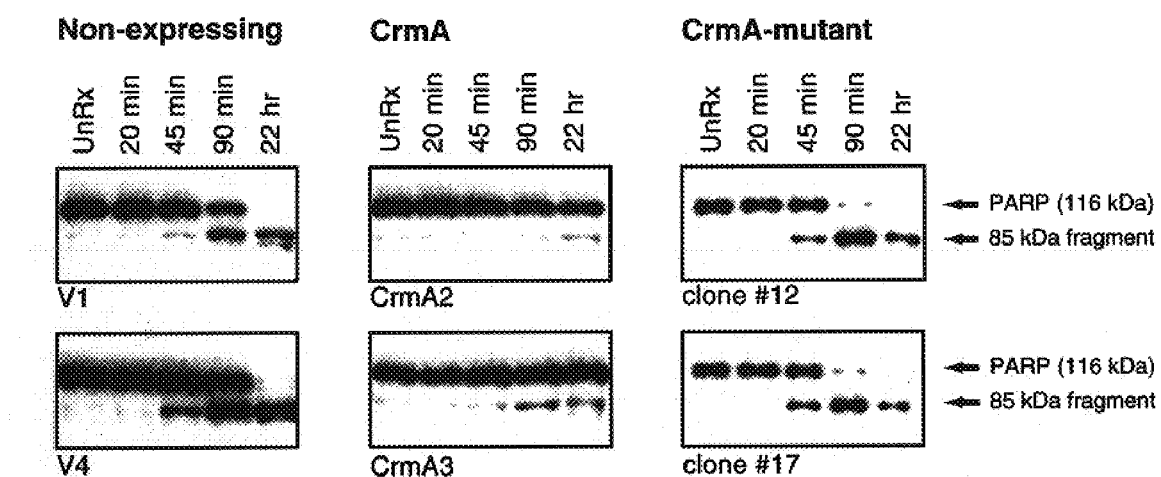
Figure 6C:
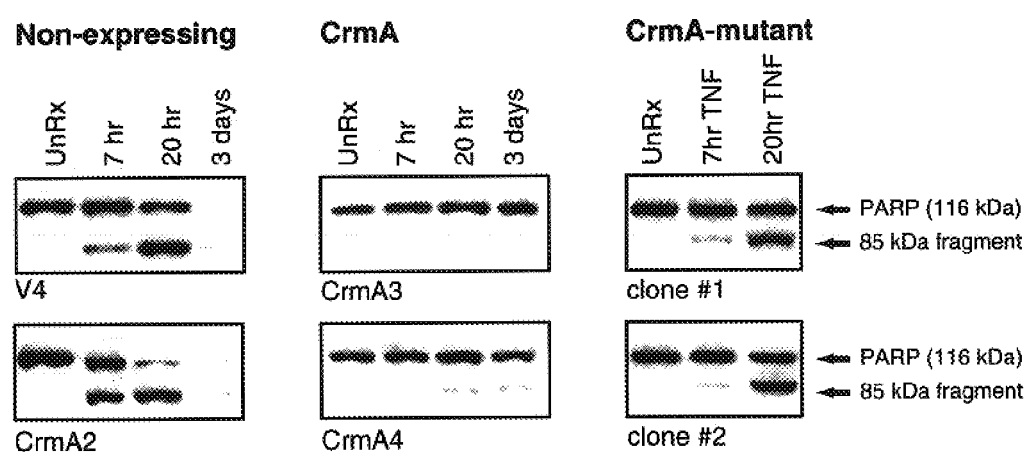

FIGS. 6A through 6C: In FIG. 6A, CrmA or CrmA-mutant is expressed in stably transfected clones. The left panel shows clonal BJAB cell lines stably transfected with either vector control (BJAB V1, BJAB V4), CrmA (BJAB CrmA2, BJAB CrmA3) or CrmA-mutant (BJAB CrmA-mutant #12, BJAB CrmA-mutant #17) expression constructs that were analyzed by Western blotting using an anti-CrmA antiserum. In the right panel, clonal MCF7 cell lines stably transfected with either vector control (MCF7 V4), CrmA (MCF7 CrmA2, MCF7 CrmA3, MCF7 CrmA4) or CrmA-mutant (CrmA-mutant #1, CrmA-mutant #2) expression constructs were similarly analyzed.

FIG. 6B shows PARP cleavage to the 85 kDa fragment during Fas-induced apoptosis is inhibited by CrmA but not by CrmA-mutant. Clonal BJAB transfectants not expressing CrmA (BJAB V1, BJAB V4), expressing CrmA (BJAB CrmA2, BJAB CrmA3) or expressing CrmA-mutant (BJAB CrmA-mutant #12, BJAB CrmA-mutant #17) were treated with agonist anti-Fas (250 ng/ml) antibody for the indicated time periods and lysates were prepared and analyzed by Western blot using the anti-PARP monoclonal antibody C-2-10.

FIG. 6C shows PARP cleavage to the 85 kDa fragment during TNF-induced apoptosis is inhibited by CrmA but not by CrmA-mutant. Clonal MCF7 transfectants not expressing CrmA (MCF7 V4, MCF7 CrmA2), expressing CrmA (MCF7 CrmA3, MCF7 CrmA4) or expressing CrmA-mutant (MCF7 CrmA-mutant #1, MCF7 CrmA-mutant #2) were treated with TNF (40 ng/ml) for the indicated time periods and lysates prepared and analyzed by Western blot using the anti-PARP monoclonal antibody C-2-10.

Figure 7A:
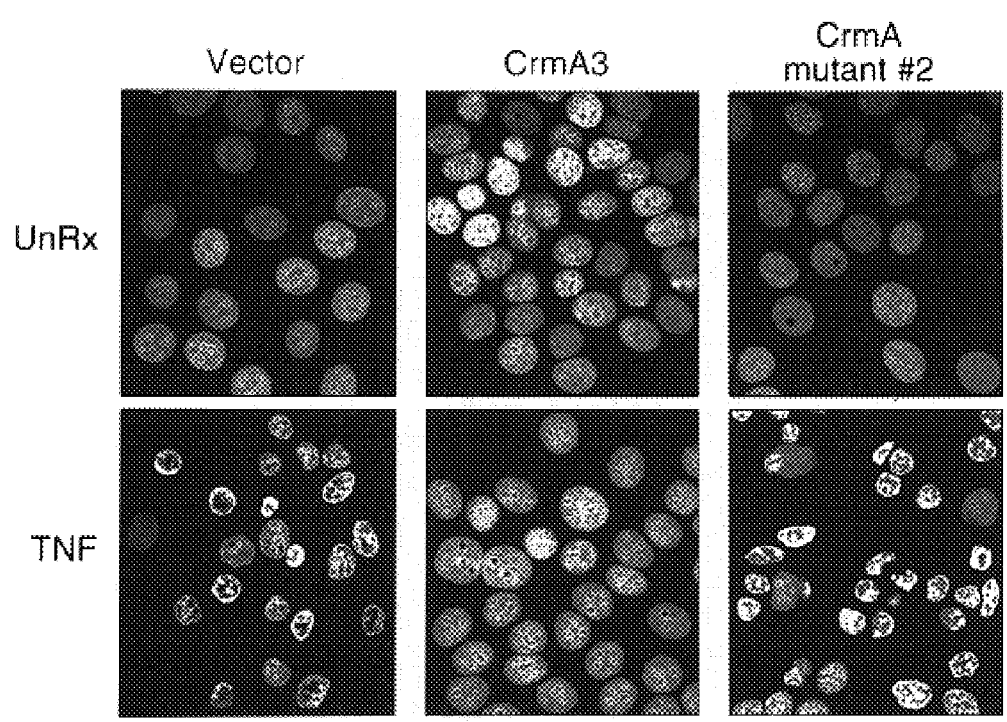
Figure 7B:
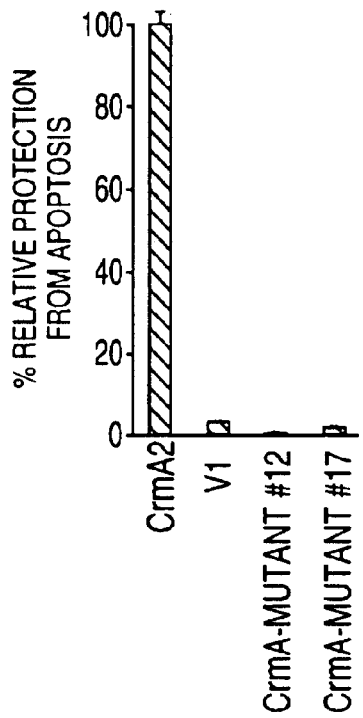
Figure 7C:
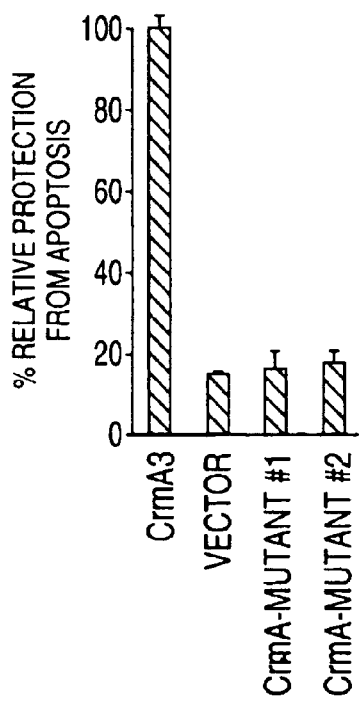

FIGS. 7A through 7C shows that CrmA, but not CrmA-mutant, blocks Fas-and TNF-induced cell death. In FIG. 7A, MCF7 stably transfected clones were either kept untreated (UnRx) or treated with TNF (40 ng/ml) for 18 hours following which cells were fixed and stained with propidium iodide and nuclear morphology examined by confocal microscopy. CrmA afforded significant protection from TNF-induced apoptosis, whereas both vector-transfected and CrmA-mutant expressing lines were sensitive to TNF-induced apoptosis. In FIG. 7B, the indicated BJAB stably transfected clones were quantitatively assessed for their sensitivity to Fas-induced PCD using an acridine orange-based apoptosis assay as described below. CrmA-mutant expressing cell lines were uniformly sensitive, whereas CrmA expression afforded significant protection. In FIG. 7C, the indicated MCF7 stably transfected clones were quantitatively assessed for their susceptibility to TNF-induced cell death as described in the experimental section below.

FIGS. 8A through 8C (SEQ ID NO: 3 and SEQ ID NO: 4) shows the nucleic acid sequence and corresponding amino acid sequence of the cowpox CrmA gene and gene product.

DETAILED DESCRIPTION OF THE INVENTION

This invention provides a purified and recombinantly produced protease, designated Yama, which is involved in the mammalian cell death pathway as well as nucleic acids that encode these proteases. It has been demonstrate that purified Yama is a zymogen which, upon activation, assumes a proteolytically competent form that cleaves poly(ADP-ribose) polymerase (PARP) to the signature 85 kDa apoptotic fragment. PARP has been identified as a death substrate which is specifically cleaved during apoptosis. Kaufmann et al. (1989) *Cancer Res.* 49:5870–5878 and (1993) 53:3976–3985 reports that the 116 kDa nuclear protein was specifically cleaved to produce an 85 kDa fragment in many forms of PCD, including that induced by chemotherapeutic drugs in cell lines and by dexamethasone in thymocytes. It was later reported by Lazebnik in *Nature* (1994) 371:346–347 in a cell-free system that cleavage occurred C-terminal to Asp, and that the protease responsible resembled ICE in its susceptibility to chemical inhibitors but was distinct from ICE, since purified ICE did not cleave PARP. Yama is further characterized in that its proteolytic activity and apoptotic activity are inhibited by purified CrmA but not by an equivalent quantity of an inactive point mutant of CrmA. As shown in detail in the experimental section below, CrmA blocked the proteolytic cleavage of PARP in cells induced to undergo apoptosis.

Definitions

The terms "proteins", "peptides" and "polypeptides" are used interchangeably and are intended to include purified and recombinantly produced molecules containing amino acids linearly coupled through peptide bonds. The amino acids of can be in the L or D form so long as the biological activity of the polypeptide is maintained. For example, the protein can be altered so as be secreted from the cell for recombinant production and purification. These also include proteins which are post-translationally modified by reactions that include glycosylation, acetylation and phosphorylation. Such polypeptides also include analogs, alleles and allelic variants which can contain amino acid derivatives or non-amino acid moieties that do not affect the biological or functional activity of the protein as compared to wild-type or naturally occurring protein. The term amino acid refers both to the naturally occurring amino acids and their derivatives, such as TyrMe and PheCl, as well as other moieties characterized by the presence of both an available carboxyl group and an amine group. Non-amino acid moieties which can be contained in such polypeptides include, for example, amino acid mimicking structures. Mimicking structures are those structures which exhibit substantially the same spatial arrangement of functional groups as amino acids but do not necessarily have both the a-amino and a-carboxyl groups characteristic of amino acids.

"Muteins" are proteins or polypeptides which have minor changes in amino acid sequence caused, for example, site-specific mutagenesis or other manipulations; by errors in transcription or translation; or which are prepared synthetically by rational design. These minor alterations result in amino acid sequences wherein the biological activity of the protein or polypeptide is altered as compared to wild-type or naturally occurring polypeptide or protein. Examples of muteins include the CrmA mutant and the Yama mutant described herein.

As used herein, the term "peptide bond" or "peptide linkage" refers to an amide linkage between a carboxyl group of one amino acid and the a-amino group of another amino acid.

As used herein, the term "hydrophobic" is intended to include those amino acids, amino acid derivatives, amino acid mimics and chemical moieties which are non-polar. Hydrophobic amino acids include Phe, Val, Trp, Ile and Leu. As used herein, the term "positively charged amino acid" refers to those amino acids, amino acid derivatives, amino acid mimics and chemical moieties which are positively charged. Positively charged amino acids include, for example, Lys, Arg and His.

"Purified" when referring to a protein or polypeptide, are distinguishable from native or naturally occurring proteins or polypeptides because they exist in a purified state. These "purified" proteins or polypeptides, or any of the intended variations as described herein, shall mean that the compound or molecule is substantially free of contaminants normally associated with the compound in its native or natural environment. The terms "substantially pure" and "isolated" are not intended to exclude mixtures of polynucleotides or polypeptides with substances that are not associated with the polynucleotides or polypeptides in nature.

"Native" polypeptides, proteins, or nucleic acid molecules refer that those recovered from a source occurring in nature or "wild-type".

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, *Remington's Pharm. Sci.*, 15th Ed. (Mack Publ. Co., Easton 1975)).

The term "nucleic acid" means single and double stranded DNA, cDNA, genome-derived DNA, and RNA, as well as the positive and negative strand of the nucleic acid which are complements of each other, including anti-sense RNA. A "nucleic acid molecule" or polynucleotide refers to a polymeric form of nucleotides of any length, either ribonucleotides or deoxyribonucleotides, or analogs thereof. It also includes known types of modifications, for example labels which are known in the art (e.g., Sambrook, et al.(1989) infra.), methylation, "caps", substitution of one or more of the naturally occurring nucleotides with an analog, internucleotide modifications such as, for example, those with uncharged linkages (e.g., methyl carbamate, etc.), those containing pendant moieties, ,such as for example, proteins (including for e.g., nuclease, toxins, antibodies, signal peptides, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. The polynucleotide may be chemically or biochemically modified or contain non-natural or derivatized nucleotide bases. The nucleotides may be complementary to the mRNA encoding the polypeptides. These complementary nucleotides include, but are not limited to, nucleotides capable of forming triple helices and antisense nucleotides. Recombinant polynucleotides comprising sequences otherwise not naturally occurring are also provided by this invention, as are alterations of wild type polypeptide sequences, including but not limited to, those due to deletion, insertion, substitution of one or more nucleotides or by fusion to other polynucleotide sequences.

A polynucleotide is said to "encode" a polypeptide it, in its native state or when manipulated by methods well known to those skilled in the art, it can be transcribed and/or translated to produce a polypeptide or mature protein. Thus, the term polynucleotide shall include, in addition to coding sequences, processing sequences and other sequences which do not code for amino acids of the mature protein. The anti-sense strand of such a polynucleotide is also said to encode the sequence.

The term "recombinant" polynucleotide or DNA refers to a polynucleotide which is made by the combination of two otherwise separated segments of sequence accomplished by the artificial manipulation of isolated segments of DNA by genetic engineering techniques or by chemical synthesis. In so doing one may join together DNA segments of desired functions to generate a desired combination of functions.

An "analog" of DNA, RNA or a polynucleotide, refers to a macromolecule resembling naturally occurring polynucleotides in form and/or function (particularly in the ability to engage in sequence-specific hydrogen bonding to base pairs on a complementary polynucleotide sequence) but which differs from DNA or RNA in, for example, the possession of an unusual or non-natural base or an altered backbone. See for example, Uhlmann et al. (1990) *Chemical Reviews* 90:543–584.

"Isolated" when referring to a nucleic acid molecule, means separated from other cellular components normally associated with native or wild-type DNA or RNA intracellularly.

An "antisense" copy of a particular polynucleotide refers to a complementary sequence that is capable of hydrogen bonding to the polynucleotide and can therefor, be capable of modulating expression of the polynucleotide. These are DNA, RNA or analogs thereof, including analogs having altered backbones, as described above. The polynucleotide to which the antisense copy binds may be in singe-stranded form or in double-stranded form.

As used herein, the term "operatively linked" means that the DNA molecule is positioned relative to the necessary regulation sequences, e.g., a promoter or enhancer, such that a promoter will direct transcription of RNA off the DNA molecule in a stable or transient manner.

"Vector" means a self-replicating nucleic acid molecule that transfers an inserted nucleic acid molecule into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above functions.

"Host cell" is intended to include any individual cell or cell culture which can be or have been recipients for vectors or the incorporation of exogenous nucleic acid molecules and/or proteins. It also is intended to include progeny of a single cell, and the progeny may not necessarily be completely identical (in morphology or in genomic or total DNA complement) to the original parent cell due to natural, accidental, or deliberate mutation.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody (as defined above) and its binding partner or ligand.

A "suitable cell" for the purposes of this invention is one that includes but is not limited to a cell expressing the Fas receptor, e.g., a bone marrow cell, endothelial cell, breast carcinoma cell, fibroblast cell, epithelial cell, epithelial tumor cell (see Spriggs, D. R. et al. (1988) *J. Clin. Inves.* 81:455–460) T cell (TCR$^+$, CD8$^+$ or CD4$^+$ T cells) peripheral blood lymphocyte, colon cell, small intestine cell, ovarian cell, testis cell, prostate cell, thymic cell, spleen cell, kidney cell, liver cell, lung cell, brain cell and monocytes. Because the Fas (APO-1/CD95) cell surface receptor is a member of the nerve growth factor (NGF)/tumor necrosis factor (TNF) receptor superfamily, any cell having a receptor of this family is intended to be encompassed by the scope of this invention. Fas and TNF receptor expression also has been identified on numerous tissues, see for example Watanabe-Fukunaga et al. (1992) *J. Immun.* 148:1049–1054 and Owen-Schaub, L. B. et al. (1994) *Cancer Res.* 54:1580–1586; Dhein et al. (1995) *Nature* 373:438–441; Brunner et al. (1995) *Nature* 373:441–444; and Ju et al. (1995) *Nature* 373:444–448. Assays for identifying additional "suitable" cells sensitive to induction or activation, e.g., TCR-, TNF- or Fas-related apoptosis, are well known to those of skill in the art. (See for example, Opipairi, et al. *J. Biol. Chem.* (1992) 267:12424–12427; Yonehara et al. *J. Exo. Med.* (1989) 169:1747–1756; Dhein et al. (1995) supra; Brunner et al. (1995) supra and Ju et al. (1995) supra). The cells can be mammalian cells or animal cells, such as guinea pig cells, rabbit cells, simian cells, mouse cells, rat cells, chicken cells or human cells. They can be continuously cultured or isolated from an animal or human. In a separate embodiment of this invention, neurological cells are specifically excluded.

When applied to apoptosis, the terms "preventing" or "inhibiting" are intended to mean a reduction in number of cells dying or a prolongation in the the survival time of the cell. They also are intended to mean a diminution in the appearance or a delay in the appearance of morphological and/or biochemical changes normally associated with apoptosis. Accordingly, "augmentation" of apoptotic cell death means an increase in the total number of cells dying or reduction of the survival time of the cell. "Augmentation" also means an reduction in the time to the appearance of the morphological and/or biochemical changes normally associated with apoptosis after contacting the cells with the apoptotic agent.

Throughout this application, various publications, patents and published patent applications are referred to by an identifying citation. The disclosures of these publications, patents and published patent applications are hereby incorporated by reference into this application to more fully describe the state of the art to which this invention pertains.

Proteins and Polypeptides

This invention provides proteins or polypeptides, purified from a native environment or recombinantly obtained, designated PRO-Yama, p20 Yama p11 Yama activated YAMA, and mutant Yama. Unless specifically identified, the term Yama protein or polypeptide is to include all forms described herein. The proteins and polypeptides can be purified from an animal source such as rat, chicken, human and mouse. The recombinant forms are obtainable from a number of procaryotic and eucaryotic recombinant systems. This invention further provides a mutant CrmA protein and polynucleotide coding the protein which does not inhibit apoptosis.

Pro-Yama is a zymogen which upon "activation" cleaves PARP to an 85 kDa form. In one embodiment, PRO-YAMA has an apparent molecular weight of about 32 kDa as determined on PAGE. In a separate embodiment, it has the 277 amino acid sequence shown in FIG. 1B. Pro-Yama consists of two subunits designated herein p20 Yama and p11 Yama. Pro-Yama is cleavable by ICE following an aspartic acid to form the p20 and p11 subunits. Accordingly, this invention also provides p20 Yama and p11 Yama purified from a native environment or obtained recombinantly. p20 Yama and p11 Yama are heterodimeric polypeptides which, in combination, are characterized in having the biological or functional ability to modulate cellular function associated with Fas receptor pathway such as Fas-associated apoptosis. In particular, p20 Yama and p11 Yama heterodimer promotes apoptosis in a suitable cell, the activity of which is inhibitable by CrmA but not mutant CrmA. They also form an inhibitory complex with CrmA but not mutant CrmA.

Apoptosis has been equated with programmed cell death (PCD) and can be detected and monitored by a number of morphological and biochemical changes. The methods which are useful to monitor and detect these changes include light microscopy, a measurement between potential and actual tumor doubling times, loss of radiolabeled DNA precursors, measurement and of DNA fragmentation, measurement by FCM. These methods are reviewed Vermes and Haanen, "Apoptosis and Programmed Cell Death in Health and Disease" *Adv. in Clin. Chem.* (1994) 31:177–246, and the references cited therein. Light microscopy and the measurement of the potential tumor doubling time versus the actual tumor volume doubling time are most applicable in mammalian pathology. "Inhibition" when used in this context, means a reduction in the number of cells undergoing apoptosis or PCD or an increase in survival time or growth rate of a cell or population of treated cells as compared to a control population. "Augmentation" means an increase in the number of cells undergoing apoptosis or PCD or a decrease in survival time or growth rate of a cell or population of treated cells as compared to a control population. A "treated cell" is a cell or a population of cells which have been exposed to the protein or antibody or have inserted therein by any number of methods a nucleic acid molecule of this invention.

As used herein, a pro-Yama protein an activated Yama protein, p20 Yama and p11 Yama are intended to include wild-type or naturally occurring protein, as well as muteins (e.g., Yama and CrmA), analogs and fragments thereof. In some embodiments, the term also includes anti-Yama antibodies and anti-idiotypic antibodies.

In one embodiment of this invention, overexpression of the DNA encoding an activated Yama protein promotes apoptosis. Examples of such proteins include, but are not limited to p20 Yama and p11 Yama. In a separate embodiment, the biological activity of the p20 or p11 Yama protein or its equivalent is inhibitable by CrmA but not the mutant CrmA described herein. The CrmA gene or nucleic acid can be isolated from natural or native sources as described in Pickup et al. (1986) PNAS 83:7698–7702. One of skill in the art can determine when and if the biological activity of a protein is inhibitable by CrmA using the method disclosed in Tewari et al. (1995) *J. Biol. Chem.* 270:3255–3260) or the methods disclosed in Experiments I through III, below.

Yama and Yama subunits can be purified from a suitable cell lysate by using epitope tagged versions highly expressed in 293T (ATCC) cells using the method disclosed in Chiang and Roeder (1993) *Peptide Research* 6(2):62–64.

Also provided by this invention are polypeptide fragments of purified or recombinantly produced Pro-Yama, p20 Yama or p11 Yama or the protein having the amino acid sequence shown in FIG. 1B. These peptides are characterized by either being activated to an apoptotic promoting form (PRO-Yama) or being able to promote apoptosis in an activated cell.

It is understood that functional equivalents of the Yama proteins identified above also are within the scope of this invention, for example the Yama fusion protein 6xHis-Yama or those containing chemical structures other than amino acids which functionally mimic the biological activity of any purified PRO-Yama, its allelic variant, purified p20 Yama, purified p11 Yama, the recombinant homologs thereof or the protein having the amino acid sequence shown in FIG. 1B ("analogs") which retain the biological activity of the corresponding purified or recombinant protein or polypeptide. An additional example of an analog is a protein or polypeptide containing a distinct protein or polypeptide joined to Yama or fragments thereof, e.g., a GST fusion protein, the equivalents which vary the primary sequence of protein of this invention from the amino acid sequence provided in FIG. 1B. However, in one embodiment of this invention, the protein designated CPP32β is specifically excluded. (See Fernandes-Alnemri, et al. (1994) *J. Biol. Chem.* 269:30761–30764), as well as ICE, Ced-3 and Nedd2.

An agent characterized by having the ability to inhibit the binding of p20 and/or p11 Yama to CrmA is further provided by this invention. Such agents include, but are not limited to, an anti-CrmA antibody or a dominant inhibitory fragment of any of CrmA, p20, p11 or PRO-Yama. A "dominant inhibitory fragment" is intended to include but is not limited to a mutein which irreversibly binds intracellular CrmA, p20 and p11 Yama heterodimeric complex, respectively. Example of dominant inhibitory muteins of Yama are those in which the functionally important cysteine sequence QACRG in p20 and PRO-Yama is mutated to alanine or methionine. These mutants have lost their apoptotic capacity but still bind their substrates thereby blocking endogenous native Yama and its biological activity or function. These Yama muteins can be made by using the amino acid sequence provided in FIG. 1B and a modification of the method provided in Experiment IX and Higuchi et al. (1988) infra.

The proteins and polypeptides of this invention are obtainable by a number of processes well known to those of skill in the art, which include purification, chemical synthesis and recombinant methods. Full length PRO-Yama, p20 Yama and pl Yama proteins can be purified from a Fas+ cell or tissue lysate using methods such as immunoprecipitation with an appropriate antibody, and standard techniques such as gel filtration, ion-exchange, reversed-phase, and affinity chromatography. For such methodology, see for example Deutscher et al., *Guide to Protein Purification: Methods in Enzymology* (1990) Vol. 182, Academic Press. Accordingly, this invention also provides the processes for obtaining the proteins and polypeptides of this invention as well as the products obtainable and obtained by these processes.

The proteins and polypeptides also can be obtained by chemical synthesis using a commercially available automated peptide synthesizer such as those manufactured by Applied Biosystems, Inc., Model 430A or 431A, Foster City, Calif. and the amino acid sequence provided in FIG. 1B and FIG. 8. The synthesized protein or polypeptide can be precipitated and further purified, for example by high performance liquid chromatography (HPLC). Accordingly, this invention also provides a process for chemically synthesizing the proteins of this invention by providing the sequence of the protein (e.g., FIG. 1B for Yama and FIGS. 3A and 8 for mutant CrmA) and reagents, such as amino acids and enzymes and linking together the amino acids in the proper orientation and linear sequence.

Alternatively, the proteins and polypeptides can be obtained by well-known recombinant methods as described, for example, in Sambrook et al., *Molecular Cloning: A Laboratory Manual* 2d ed. (Cold Spring Harbor Laboratory (1989)) using the host cell and vector systems described and exemplified below. This invention further provides a process for producing a Pro-Yama or p20 or p11 Yama protein, analog, mutein or fragment thereof, by growing a host cell containing a nucleic acid molecule encoding the protein, the nucleic acid being operatively linked to a promoter of RNA transcription. The host cell is grown under suitable conditions such that the nucleic acid is transcribed and translated into protein. In a separate embodiment, the protein is further purified.

Also provided by this invention are the proteins described herein conjugated to a detectable agent for use in diagnostic methods. For example, detectably labeled proteins and polypeptides containing the p20 and p11 heterodimeric Yama can be bound to a column and used for the detection and purification of CrmA. They also are useful as immunogens for the production of antibodies as described below. The proteins and fragments of this invention are useful in an in vitro assay system to screen for agents or drugs which either inhibit or augment the Fas-related function such as apoptosis and to test possible therapies for disorders associated with this pathway, e.g., lps, immunosuppression, depletion of CD4+ T cells, and carcinogenesis.

More specifically, the in vitro cellular method comprises providing cell cultures or tissue cultures having either a cell surface receptor that mediates apoptosis such as a TCR, the TNF receptor or the Fas receptor. The cells are cultured under conditions (temperature, growth or culture medium and gas ($CO_2$)) and for an appropriate amount of time to attain exponential proliferation without density dependent constraints. The cells are then exposed to preliminary conditions necessary for apoptosis, for example an effective amount of an inducing agent, e.g., a TCR ligand, HIV, SIV, TNF, or a Fas ligand such as an anti-Fas antibody is added to the culture. Anti-Fas antibodies and mitogens (ConA) are well known to those of skill in the art. (Itoh, N. et al. (1991) *Cell* 66:233–243 and Yonehara et al. (1989) *J. Exp. Med.* (1989) 169:1747–1756). These cells are now "induced" to apoptosis. The cells are again cultured under suitable temperature and time conditions. In one embodiment, HIV or SIV is added to the culture. In other embodiments, a drug or agent to be tested is added in varying concentrations at a time that is simultaneous with, prior to, or after the inducing agent.

Pro-Yama nucleic acid molecule or protein is then added to the culture in an effective amount and under conditions that the cells internalize the nucleic acid or protein. In some embodiments, an effective amount of ICE or ICE nucleic acid is added to activate PRO-Yama. The cells are cultured under suitable temperature and time conditions to induce apoptosis. The cells are separated into two samples. In the first set, the CrmA nucleic acid or protein can be added prior to, simultaneously with, or after, the agent to be tested. The cells are assayed for apoptotic activity using methods well known to those of skill in the art and described herein. It is apparent to those of skill in the art that at least two separate culture of cells must be treated and maintained as the test population. One is maintained without receiving an inducing agent to determine background release and the second with the receiving the agent to be tested. The second population of cells acts as a control.

The use of the compositions and methods in vitro provides a powerful bioassay for screening for drugs which are agonists or antagonists of CrmA and Yama function in these cells. Thus, one can screen for drugs having similar or enhanced ability to prevent or inhibit apoptosis as CrmA or the ability to induce apoptosis as Yama. One of skill in the art can determine when the method has been successfully performed by noting the absence of apoptotic morphological changes or more simply, by the absence of cell death. The in vitro method further provides an assay to determine if the method of this invention is useful to treat a subject's pathological condition or disease that has been linked to apoptotic cell death in the individual.

For example, a T cell hybridoma cell line such as Jurkat can be stably transfected with the CrmA expression construct, expression vector containing pro-Yama, activated Yama, CrmA or mutant Yama, or vector alone and clonal cell lines derived. Transfection of Jurkat cell by electroporation can be performed as described in Dixit et al. *J. Biol. Chem.* (1993) 263:5032–5039. The cells are $^{51}$Cr-labeled and plated ($5 \times 10^5$ /ml) on untreated or anti-CD3 (available from the cell line 145-2C11 (ATCC)) treated tissue culture plastic plates. Cells cultured on uncoated cells are used to determine background release. The percentage cell death will be determined at various times after culture by the formula: c.p.m. released from the experimental group minus c.p.m. of background release divided by c.p.m. released by 0.5% Triton X-100 (complete lysis)—c.p.m. of background release. Agents are then added to the culture to determine their effect on apoptosis, with and without exogenously added CrmA, Yama and mutant Yama nucleic acids or proteins. Using the method described above, various agents can be tested for their, ability to inhibit, prevent or augment apoptosis.

In a separate embodiment, the T cell line designated CEM (ATCC) is obtained and used because it has been shown to undergo PCD upon infection with HIV. CEM cells are transfected by electroporation with the CrmA expression construct and vector alone as control. Clonal lines are derived and infected at various multiplicity of infection ratios with HIV. Cytopathic effect is assayed by microscopic observation and apoptosis quantitated following propidium iodine staining. Using the method described above, various agents can be tested for their ability to inhibit or prevent apoptosis.

The proteins of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant which is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides.

This invention also provides a pharmaceutical composition comprising any of a protein, analog, mutein, polypeptide fragment, antibody, antibody fragment or anti-idiotipic antibody of this invention, alone or in combination with each other or other agents, and an acceptable carrier. These compositions are useful for various diagnostic and therapeutic methods.

Nucleic Acids

Nucleic acid molecules and isolated nucleic acid molecules which encode amino acid sequences corresponding to a Yama protein, mutein, CrmA mutein analog, p20 or p11 polypeptide, antibodies, anti-idiotypic antibody and antibody fragments, as well as complements of these sequences, are further provided by this invention. In addition to the sequences shown in FIGS. 1, 3A and 8, this invention also provides the anti-sense polynucleotide stand, e.g. antisense RNA. One can obtain an antisense RNA using the sequence provided in FIG. 1, for example, and the methodology described in Vander Krol et al. (1988) *BioTechniques* 6:958. Unless specifically identified the term "Yama" nucleic acid is to encompass all the Yama nucleic acids described herein.

In one aspect of this invention, the nucleic acid molecule encoding Yama protein or polypeptide is defined to be any of the sequence or parts thereof shown in FIG. 1A. Also included within the scope of this invention are the DNA or RNA complements of these nucleic acid molecules.

The invention also encompasses nucleic acid molecules which differ from that of the nucleic acid molecules described above, but which produce the same phenotypic effect, such as an allele. These altered, but phenotypically equivalent nucleic acid molecules are referred to "equivalent nucleic acids." This invention also encompasses nucleic acid molecules characterized by changes in non-coding regions that do not alter the phenotype of the polypeptide produced therefrom when compared to the nucleic acid molecule herein. This invention further encompasses nucleic acid molecules which hybridize to the nucleic acid molecules of the subject invention under stringent conditions. Also within the scope of this invention are nucleic acids having a sequence altered from that shown in FIG. 1A but produce a protein having enhanced or diminished biological activity.

In one embodiment, specifically excluded are the nucleic acid molecules encoding the protein designated CPP32β (Fernanes-Alnemri et al. (1994) supra), Ced-3, ICE and Nedd2.

The nucleic acid molecules can be conjugated to a detectable marker, e.g., an enzymatic label or a radioisotope for detection of nucleic acid and/or expression of the gene encoding Yama in a cell. Briefly, this invention further provides a method for detecting a single-stranded nucleic acid molecule encoding an amino acid sequence which is at least a portion of Yama by contacting single-stranded nucleic acid molecules with a labeled, single-stranded nucleic acid molecule (a probe) which is complementary to a single-stranded nucleic acid molecule encoding an amino acid sequence which is at least a portion of the Yama protein under conditions permitting hybridization (preferably stringent hybridization conditions) of complementary single-stranded nucleic acid molecules. Hybridized nucleic acid molecules are separated from single-stranded nucleic acid molecules. The hybridized molecules are detected using methods well known to those of skill in the art and set forth, for example, in Sambrook (1989) supra.

The nucleic acid molecules of this invention can be isolated using the technique described in the experimental section described below or replicated using PCR (Perkin-Elmer). For example, the sequence can be chemically replicated using PCR (Perkin-Elmer) which in combination with the synthesis of oligonucleotides, allows easy reproduction of DNA sequences. The PCR technology is the subject matter of U.S. Pat. Nos. 4,683,195, 4,800,159, 4,754,065, and 4,683,202 and described in *PCR: The Polymerase Chain Reaction* Mullis et al. eds, Birkhauser Press, Boston (1994) and references cited therein. Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the nucleic acid into a suitable replication vector and insert the vector into a suitable host cell (a human B cell or BJAB or 293 T cell) for replication and amplification. The DNA so amplified can be isolated from the cell by methods well known to those of skill in the art. A process for obtaining nucleic acid molecules by this method is further provided herein as well as the nucleic acid molecules so obtained.

RNA can be obtained by using the isolated DNA and operatively linking it to a control region appropriate for the host cell and inserting it into a host cell. A suitable cell for this purpose includes but is not limited to a human B cell, BJAB or 293T cell. The DNA can be inserted by any appropriate method, e.g., by the use of an appropriate insertion vector or by electroporation. When the cell replicates and the DNA is transcribed into RNA; the RNA can then be isolated using methods well known to those of skill in the art, for example, as set forth in Sambrook et al. (1989) supra.

The invention further provides the nucleic acid molecule operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted nucleic acid molecule. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see *Gene Expression Technology*, Goeddel ed., Academic Press, Inc. (1991) and references cited therein and *Vectors: Essential Data Series* Gacesa and Ramji, eds., John Wiley & Sons, N.Y. (1994), which contains maps, functional properties, commercial suppliers and a reference to GenEMBL accession numbers for various suitable vectors. Preferable, these vectors are capable of transcribing RNA in vitro or in vivo.

Fragments of the polynucleotide sequence shown in FIG. 1A also are encompassed by this invention, preferably at least 10 nucleotides and more preferably having at least 18 nucleotides. These are useful as hybridization probes.

In one embodiment, these fragments are nucleic acid molecules that encode proteins designated p20 Yama and p11 Yama. The nucleic acid molecules encode polypeptides which heterodimerize and bind CrmA and induce apoptosis in an activated cell. This and additional fragments of this invention are useful to code for proteins having diagnostic and therapeutic utilities as described herein as well as probes to identify transcripts of the protein which may or may not be present. These nucleic acid fragments can by prepared, for example, by restriction enzyme digestion of the nucleic acid molecule of FIG. 1A and then labeled with a detectable marker such as a radioisotope using well known methods. Alternatively, random fragments can be generated using nick translation of the molecule. For methodology for the preparation and labeling of such fragments, see Sambrook et al., *Molecular Cloning: A Laboratory Manual* Cold Spring Harbor Press, Cold Spring Harbor, N.Y. (1989). Polynucleotide fragments also are useful to generate novel peptides. These peptides, in turn, are useful as immunogens for the generation of polyclonal and monoclonal antibodies.

As noted above, a nucleic acid molecule of this invention can be operatively linked to a promoter, either an inducible or non-inducible promoter, of RNA transcription. These nucleic acid molecules are useful for the recombinant production of Yama proteins and polypeptides or as vectors for use in gene therapy. Accordingly, this invention also provides a vector (insertion, replication or expression vector) having inserted therein a nucleic acid molecule described above, for example, a viral vector, such as bacteriophage, baculovirus and retrovirus, or cosmids, plasmids, YACS, yeast and other recombinant vectors. Nucleic acid molecules are inserted into vector genomes by methods well known in the art. For example, insert and vector DNA can both be exposed to a restriction enzyme to create complementary ends on both molecules that base pair with each other and which are then joined together with a ligase. Alternatively, synthetic nucleic acid linkers can be ligated to the insert DNA that correspond to a restriction site in the vector DNA, which is then digested with a restriction enzyme that recognizes a particular nucleotide sequence. Additionally, an oligonucleotide containing a termination codon and an appropriate restriction site can be ligated for insertion into a vector containing, for example, some or all of the following: a selectable marker gene, such as neomycin gene for selection of stable or transient transfectants in mammalian cells; enhancer/promoter sequences from the immediate early gene of human cytomegalovirus (CMV) for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and anti-sense RNA.

An additional example of a vector construct of this invention is a bacterial expression vector including a promoter such as the lac promoter and for transcription initiation, the Shine-Dalgarno sequence and the start codon AUG (Sambrook et al. (1989) supra). Similarly, a eucaryotic expression vector is a heterologous or homologous promoter for RNA polymerase II, a downstream polyadenylation signal, the start codon AUG, and a termination codon for detachment of the ribosome. Such vectors can be obtained commercially or assembled using the sequences described herein. In one embodiment of this invention, the expression vector is to be specifically targeted to T cells. For these methods, it intended that the CrmA DNA be operatively linked to a promoter that is highly active in T cells. Such promoters include, but are not limited to: IFN-τ; IL-2; IL-3; IL-4; IL-5; IL-9; IL-10; TFN-β; GM-CSF; CD4, CD8 and the IL-2 promoter.

Expression vectors containing these nucleic acids are useful to obtain host vector systems to produce Yama proteins and polypeptides and the mutant CrmA described herein. It is implied that these expression vectors must be replicable in the host organisms either as episomes or as an integral part of the chromosomal DNA. Suitable expression vectors include viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a procaryotic or a eucaryotic cell and the host cell replicates, the protein can be recombinantly produced. Suitable host cells will depend on the vector and can include mammalian cells, animal cells, human cells, simian cells, insect cells, yeast cells, and bacterial cells constructed using well known methods. See Sambrook et al. (1989) supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; or DEAE-dextran; electroporation; or microinjection. See Sambrook et al. (1989) supra for this methodology. Thus, this invention also provides a host cell, e.g. a mammalian cell, an animal cell (rat or mouse), a human cell, or a bacterial cell, containing a nucleic acid molecule encoding a Yama protein or polypeptide or an Yama protein or polypeptide or antibody.

Using the host vector system described above, a process of producing and/or obtaining recombinant Yama, analog, mutein, or anti-Yama antibody or active fragments thereof or mutant CrmA is provided by growing the host cells described herein under suitable conditions such that the nucleic acid encoding Yama or anti-Yama protein, polypeptide or antibody is expressed. Suitable conditions can be determined using methods well known to those of skill in the art, see for example, Sambrook et al., (1989) supra. The recombination products are then purified from the cellular extract. Accordingly, this invention further provides host cells containing exogenously added nucleic acid molecules of this invention as well as processes for recombinantly producing the proteins, polypeptides and antibodies of this invention by performing the above mentioned steps as well as the products so produced.

A vector containing the nucleic acid encoding Yama, anti-Yama protein, Yama antisense RNA, nucleic acid molecule encoding Yama antisense RNA or antibody also is useful for gene therapy to modulate or regulate cellular functions such as apoptosis and immune disorders mediated by the Fas pathway. The terms "Fas+ cellular function" is intended to mean cellular functions which are affected by the binding of the receptor to its extracellular ligands, i.e., alone or in combination with each other. In some instances, for example in a neoplastic or carcinoma cell, it is desirable to augment Fas+ apoptotic function to induce apoptosis. This can be achieved by introducing into the cell pro-Yama and an activating agent such as ICE or p20 and p11 heterodimeric Yama protein or nucleic acid molecules encoding polypeptides and proteins having this biological activity. In other instances, it is desirable to down-regulate Fas+ cellular function. This can be accomplished by introducing into the cell an antibody fragment which is a dominant inhibitor of p20 or p11 Yama, Yama antisense RNA (or the DNA which codes for it) or CrmA protein or the nucleic acid molecules coding for these agents. In addition, anti-sense Yama RNA can be used to inhibit production of the Pro-Yama protein. This therapy will inhibit or disable intracellular Fas signaling and therefore is a useful therapy where apoptotic cell death is to be avoided, such as in an HIV-infected T cell.

When used for gene therapy in vivo or ex vivo, a pharmaceutically acceptable vector is preferred, such as a replication-incompetent retroviral vector. Pharmaceutically acceptable vectors containing the nucleic acids of this invention can be further modified for transient or stable expression of the inserted nucleic acid molecule. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller, A. D. et al. (1989) BioTechniques 7:980–990). The methodology of using replication-incompetent retroviruses for retroviral-mediated gene transfer of gene markers is well established (Correll, et al. (1989) PNAS USA 86:8912; Bordignon (1989), PNAS USA 86:8912–52; Culver, K. (1991), PNAS USA 88:3155; and Rill, D. R. (1991) Blood 79(10):2694–700. Clinical investigations have shown that there are few or no adverse effects associated with the viral vectors, see Anderson, (1992) Science 256:808–13.

Compositions containing the nucleic acid molecules of this invention, in isolated form or contained within a vector or host cell are further provided herein. When these compositions are to be used pharmaceutically, they are combined with a pharmaceutically acceptable carrier.

Antibodies

Also provided by this invention is an antibody capable of specifically forming a complex with Pro-Yama protein activated Pro-Yama, fragments of Yama such as p20 Yama and p11 Yama or a fragment of these antibodies, as well as nucleic acid molecules encoding them. Vectors and host cells containing these nucleic acids also are encompassed by this invention. The term "antibody" includes polyclonal antibodies and monoclonal antibodies. The antibodies include, but are not limited to mouse, rat, rabbit or human antibodies.

As used herein, an "antibody" or "polyclonal antibody" means a protein that is produced in response to immunization with an antigen or receptor and that reacts with the antigen with an effective specificity and affinity for its intended purpose. The term "monoclonal antibody" means an immunoglobulin derived from a single clone of cells. All monoclonal antibodies derived from the clone are chemically and structurally identical, and specific for a single antigenic determinant. The hybridoma cell lines producing the monoclonal antibodies also are within the scope of this invention.

Laboratory methods for producing polyclonal antibodies and monoclonal antibodies, as well as deducing their corresponding nucleic acid sequences, are known in the art, see Harlow and Lane, Antibodies: A Laboratory Manual, Cold Spring Harbor Laboratory, New York (1988) U.S. Pat. No. 5,411,749 and Sambrook et al. (1989) supra. The monoclonal antibodies of this invention can be biologically produced by introducing Yama protein or a fragment thereof into an animal, e.g., a mouse or a rabbit. The antibody producing cells in the animal are isolated and fused with myeloma cells or heteromyeloma cells to produce hybrid cells or hybridomas. Accordingly, the hybridoma cells producing the monoclonal antibodies of this invention also are provided.

Thus, using the Yama protein or fragment thereof, and well known methods, one of skill in the art can produce and screen the hybridoma cells and antibodies of this invention for antibodies having the ability to bind Yama.

If a monoclonal antibody being tested binds with a Yama protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding Yama with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with Yama protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. 82:8653 or Spira et al. (1984) J. Immunol. Methods 74:307.

This invention also provides biological active fragments of the polyclonal and monoclonal antibodies described above. These "antibody fragments" retain some ability to selectively bind with its antigen or immunogen. Such antibody fragments can include, but are not limited to:

(1) Fab, the fragment which contains a monovalent antigen-binding fragment of an antibody molecule produced by digestion with the enzyme papain to yield an intact light chain and a portion of one heavy chain;

(2) Fab', the fragment of an antibody molecule obtained by treating with pepsin, followed by reduction, to yield an intact light chain and a portion of the heavy chain; two Fab' fragments are obtained per antibody molecule;

(3) F(ab')$_2$, the fragment of the antibody that is obtained by treating with the enzyme pepsin without subsequent reduction; F(ab')$_2$ is a dimer of two Fab' fragments held together by at least one disulfide bond;

(4) Fv, defined as a genetically engineered fragment containing the variable region of the light chain and the variable region of the heavy chain expressed as two chains; and (5) SCA, defined as a genetically engineered molecule containing the variable region of the light chain, the variable region of the heavy chain, linked by a suitable polypeptide linker as a genetically fused single chain molecule.

A specific example of "biologically active antibody fragment" include the CDR and VH regions of the antibodies. Methods of making these fragments are known in the art, see for example, Harlow and Lane, (1988) supra and Davies et al. (1995) *Bio/Technology* 13(5):475–479.

The antibodies of this invention also can be modified to create chimeric antibodies and humanized antibodies (Oi, et al. (1986) *BioTechniques* 4(3):214). Chimeric antibodies are those in which the various domains of the antibodies' heavy and light chains are coded for by DNA from more than one species.

The isolation of other hybridomas secreting monoclonal antibodies with the specificity of the monoclonal antibodies of the invention can also be accomplished by one of ordinary skill in the art by producing anti-idiotypic antibodies (Herlyn, et al. (1986) *Science* 232:100). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with similar idiotypes as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

As used in this invention, the term "epitope" is meant to include any determinant having specific affinity for the monoclonal antibodies of the invention. Epitopic determinants usually consist of chemically active surface groupings of molecules such as amino acids or sugar side chains and usually have specific three dimensional structural characteristics, as well as specific charge characteristics.

Also encompassed by this invention are proteins or polypeptides that have been recombinantly produced, biochemically synthesized, chemically synthesized or chemically modified, that retain the ability to bind Pro-Yama, p20 Yama or p11 Yama, or fragments thereof, corresponding native polyclonal or monoclonal antibody.

The antibodies of this invention can be linked to a detectable agent or a hapten. The complex is useful to detect the Fas receptor or Yama protein or fragments in a sample or detect agents which interfere with Yama-Fas receptor binding, using standard immunochemical techniques such as immunohistochemistry as described by Harlow and Lane (1988) supra. Examples of types of immunoassays which can utilize monoclonal antibodies of the invention are competitive and non-competitive immunoassays in either a direct or indirect format. Examples of such immunoassays are the enzyme linked immunoassay (ELISA) radioimmunoassay (RIA) and the sandwich (immunometric) assay. Detection of the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitrophenyl, pyridoxal, and fluorescein, which can react with specific anti-hapten antibodies. See Harlow and Lane (1988) supra.

The monoclonal antibodies of the invention can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, Yama may be detected by the monoclonal antibodies of the invention when present in biological fluids and tissues. Any sample of cells or tissue lysate containing a detectable amount of Yama can be used.

Compositions containing the antibodies, fragments thereof or cell lines which produce the antibodies, are encompassed by this invention. When these compositions are to be used pharmaceutically, they are combined with a pharmaceutically acceptable carrier.

Compositions

This invention also provides compositions containing any of the above-mentioned proteins, muteins, polypeptides, nucleic acid molecules, vectors, host cells antibodies and fragments thereof, and an acceptable solid or liquid carrier. When the compositions are used pharmaceutically, they are combined with a "pharmaceutically acceptable carrier" for diagnostic and therapeutic use. These compositions also can be used for the preparation of medicaments for the diagnosis and treatment of pathologies associated with the Fas receptor and apoptotic pathway.

Diagnostic and Therapeutic Utilities

The compositions described above provide the components for an assay to screen for agents and pharmaceutical compounds which are agonists or antagonists of Fas-associated apoptosis in a suitable cell. A suitable cell is one which contains the Fas/CD95 or TNF receptor or which is induced to apoptosis or PCD by an endogenous agent such as HIV, anti-TCR antibody, a Fas agonist, TNF or an anti-Fas antibody. In one embodiment, these cells constitutively and inducibly express receptors for either or both of the cytokine tumor necrosis factor (TNF) or the cell death transducing receptor Fas or TCR and which have been activated by their respective ligand. Recently, three separate groups have reported that Fas-induced apoptosis is involved in T cell death. Specifically, one group has shown that the Fas receptor, which can transduce a potent apoptotic signal when ligated, is rapidly expressed following activation on T cell hybridomas. It was suggested that the Fas receptor-ligand interaction induces cell death in a cell-autonomous manner. See Dhein et al. (1995) *Nature* 373:438–441; Brunner et al. (1995) *Nature* 373:441–444; and Ju et al. (1995) *Nature* 373:444–448.

For the purpose of illustration only, examples of suitable cells are T lymphocytes (T cells) (e.g., TCR$^+$, CD4$^+$ and CD8$^+$ T cells) leukocytes and mixed leukocyte cultures (MLC), B lymphoma cells (e.g., A202J (ATCC)), peripheral blood lymphocytes, colon cells, small intestine cells, an ovarian cells, testis cells, prostate cells, thymic cells, spleen cells, kidney cells, liver cells, neoplastic cells, carcinoma cells, lung cells or brain cells, each from a mammalian species, e.g., mouse, rat, simian or human.

As provided in more detail below, the proteins and fragments thereof are useful in a cell-free and cellular in vitro assay system to screen for agents and pharmaceutical compounds which either inhibit or augment the Fas-receptor pathway and apoptosis and to test possible therapies for disorders associated with this pathway, e.g., lps, immunosuppression, depletion of CD4$^+$ T cells, and carcinogenesis. Embryogenesis also can be modulated.

The cell free screen is performed essentially as set forth in Experiments VII and VIII below. For example, an effective amount of Pro-Yama is activated by incubating with ICE in Reaction Buffer at 37° C. Following activation, the reaction is divided into two parts. Into one part an effective amount of the agent to be tested is added. Into the second part, an effective amount of CrmA is added. Each reaction mix is incubated for approximately 30 minutes. An effective amount of PARP is added to each mix and the solutions are further incubated at 37° C. for an effective amount of time or about 2 hours. Following this incubation, a sample from each reaction mixture is analyzed by immunoblotting with anti-PARP monoclonal antibody such as C-2-10 or by gel electrophoresis to determine if the agent inhibited cleavage of PARP to its characteristic 85 kDa form. The presence of the 85 kDa form is an indication that the agent is not an inhibitory agent and the absence of the 85 kDa form is an indication that the agent is candidate for inhibiting Fas-associated functions such as apoptosis.

Also encompassed by this invention are the agents detected by these methods, the nucleic acid molecules encoding them and the use of these agents and nucleic acid molecules in the therapeutic methods described herein. As is apparent to those of skill in the art, the above compositions can be combined with instructions for use to provide a kit for a commercially available screen.

The above methods allow one also to screen for drugs having similar or enhanced ability to prevent or inhibit apoptosis as compared to CrmA, for example.

In the cellular in vitro method, suitable cell cultures or tissue cultures are provided. A suitable cell culture for this purpose is one having either a cell surface receptor that mediates apoptosis such as a TCR, the TNF receptor or the Fas receptor. The cells are cultured under conditions (temperature, growth or culture medium and gas ($CO_2$)) and for an appropriate amount of time to attain exponential proliferation without density dependent constraints. The cells are then exposed to preliminary conditions necessary for apoptosis, for example an effective amount of an inducing agent, e.g., a TCR ligand, HIV, SIV, TNF, or a Fas ligand such as an anti-Fas antibody is added to the culture. Anti-Fas antibodies and mitogens (ConA) are well known to those of skill in the art. (Itoh, N. et al. (1991) *Cell* 66:233–243 and Yonehara et al. (1989) *J. Exp. Med.* (1989) 169:1747–1756). These cells are now "induced" to apoptosis. Alternatively, the cells can be contacted with the inducing agent after transfection with the Yama nucleic acid and agent. The cells are again cultured under suitable temperature and time conditions. An effective amount of an agent which is believed to inhibit apoptosis in this system is added to the cell culture. For example, an effective amount of a nucleic acid molecule encoding Pro-Yama, p20 Yama or p11 Yama is contacted with the cell or tissue culture so as to insert the nucleic acid. Alternatively, an effective amount of the polypeptide or protein products are added to the cell culture. The cells are again cultured for expression of the inserted nucleic acid molecule. An effective amount of the agent to be tested is then added to the cell or tissue culture in varying concentrations.

Because the activity of p20 and p11 Yama is inhibitable by CrmA, a separate culture of cells which can act as a comparison is cultured under identical conditions as described above, except that CrmA nucleic acid is added to the culture rather than the agent. The CrmA nucleic acid or protein is added the culture in an effective amount and the cells are cultured under suitable temperature and time conditions to inhibit apoptosis. The CrmA nucleic acid or protein can be added prior to, simultaneously with, or after, the inducing agent.

It also is desirable to maintain an additional separate cell cultures; one which does not receive an inducing agent to determine background release and another which does not receive the agent to be tested.

Each of the samples of cells is then assayed for apoptotic activity using methods well known to those of skill in the art and described herein. An example of this screen is provided in Experiments X through XIV below.

The compositions provided herein are useful to modulate the Fas receptor pathway and cellular functions associated with this pathway by preventing or inhibiting Fas regulated apoptosis or growth and differentiation of cells. As used herein, the term "Fas-receptor mediated or modulated cellular function" is to include any cellular response or function which has been linked to the binding of Fas or Fas/TNF receptor complex to its extracellular and/or intracellular ligand. Apoptotic cell death is one such response.

Methods of modulating cellular functions such as apoptotic cell death are provided herein. These methods comprise the steps of administering to the subject, such as an animal or human, an effective amount of a Pro-Yama, activated Pro-Yama p20 or p11 nucleic acid, antibody or protein or inhibitory nucleic antibody or protein. When the cellular function is augmentation of apoptotic cell death, an effective amount of a nucleic acid molecule coding for Pro-Yama or p20 and p11 Yama or their protein products can be administered to the subject. When the cellular function is inhibition or prevention of apoptotic cell death, an effective amount of a nucleic acid molecule coding for antisense Yama RNA, an anti-Yama antibody fragment, dominant inhibitory Yama, CrmA or their protein products are administered to the subject.

When practiced in vivo, the compositions and methods are particularly useful for modulating or regulating Fas receptor induced function in a subject or an individual suffering from or predisposed to suffer from receptor-related disfunction or for maintaining T cell viability and function in a subject or an individual suffering from or predisposed to suffer from abnormal lymphocyte death, e.g. CD4+ T cell depletion associated with HIV infection. When the method is practiced in vivo in a human patient, it is unnecessary to provide the inducing agent since it is provided by the patient's immune system. When the method is practiced in vivo, the carrying vector, polypeptide, polypeptide equivalent, or expression vector can be added to a pharmaceutically acceptable carrier and systemically administered to the subject, such as a human patient or an animal such as a mouse, a guinea pig, a simian, a rabbit or a rat. Alternatively, it can be directly infused into the cell by microinjection or localized administration into a tumor. A fusion protein also can be constructed comprising the T-cell specific ligand for targeting to a T cell. Such T cell specific ligands include, but are not limited to anti-CD3, anti-CD4, anti-CD28 and anti-IL-1-receptor antibody.

This invention also is particularly useful to ward off lymphocyte death or immunosuppression in AIDS patients. By preventing or inhibiting apoptosis, not only is cell death prevented but functionality, e.g., immuno-proliferative capacity, is restored to the cell and a responsive immune system is retained or regained. Accordingly, the compositions and methods of this invention are suitably combined with compositions and methods which prevent or inhibit HIV infectivity and replication.

The method also can be practiced ex vivo using a modification of the method described in Lum et al. (1993) *Bone Marrow Transplantation* 12:565–571 or a modification of the method described in U.S. Pat. No. 5,399,346. Generally, a sample of cells such as bone marrow cells or MLC can be removed from a subject or animal using methods well known to those of skill in the art. An effective amount of the CrmA or a Yama nucleic acid molecule or expression vector is added to the cells and the cells are cultured under conditions that favor internalization of the nucleic acid by the cells. The transformed cells are then returned or reintroduced to the same subject or animal (autologous) or one of the same species (allogeneic) in an effective amount and in combination with appropriate pharmaceutical compositions and carriers.

Alternatively, fresh peripheral blood mononuclear cells (MNCS) isolated from the mammal or patient are separated from the red cells and neutrophils by Ficoll-Hypaque density gradient centrifugation. The MNCs are then washed, counted and cultured at approximately $1 \times 10^6$ cells/well in a 24 well tissue culture plates in AIM-V which consists of AIM-V (GIBCO) with 2mM glutamine, 50 U/ml penicillin, 50 μg/ml streptomycin, 2.5 μg/ml Fungizone and 25–1000 U/ml of IL-2 (Cetus). The cells are cultured at 37° C. in a humidified incubator with 5% CO.

After the T cells have begun to proliferate, an appropriate insertion vector containing a CrmA or a Yama nucleic acid molecule is contacted with the cells to insert Yama nucleic acid into the proliferating cells. Multiple transfection of the cells may be necessary. The cells are maintained for an additional 2 to 7 days with fresh medium and under conditions to return the cells to exponential growth. Approximately 0.1 to $2.5 \times 10^{10}$ T cells (or 80% of the total culture) are infused into the mammal or patient and the remaining cells can be cyropreserved for future infusions. A sample of the cells also can be removed for Southern analysis of insertion of the Yama nucleic acid molecule and its expression using northern analysis.

As used herein, the term "administering" for in vivo and ex vivo purposes means providing the subject with an effective amount of the nucleic acid molecule or polypeptide effective to modulate the Fas associated cellular function, e.g., to prevent, inhibit or augment apoptosis of the target cell. Methods of administering pharmaceutical compositions are well known to those of skill in the art and include, but are not limited to, microinjection, intravenous or parenteral administration. The compositions are intended for topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the vector used for therapy, the polypeptide or protein used for therapy, the purpose of the therapy, the target cell being treated, and the subject being treated. Single or multiple administrations can be carried out with the dose level and pattern being selected by the treating physician. For example, the compositions can be administered prior to a subject already suffering from a disease or condition that is linked to apoptosis. In this situation, an effective "therapeutic amount" of the composition is administered to prevent or at least partially arrest apoptosis and the accompanying pathology such as immunosuppression in HIV infected individuals.

However, the compositions can be administered to subjects or individuals susceptible to or at risk of developing apoptosis-related disease to prevent pathological cell death. In one embodiment, the composition can be administered to a subject susceptible to HIV-related lymphocyte disfunction to maintain lymphocyte cell function and viability. In these embodiments, a "prophylactically effective amount" of the composition is administered to maintain cellular viability and function at a level near to the pre-infection level.

It should be understood that by preventing or inhibiting unwanted cell death in a subject or individual, the compositions and methods of this invention also provide methods for treating, preventing or ameliorating the symptoms associated with a disease characterized by apoptosis of cells. Such diseases include but are not limited to AIDS, acute and chronic inflammatory disease, leukemia, myocardial infarction, stroke, traumatic brain injury, neural and muscular degenerative diseases, aging, tumor induced-cachexia and hair loss.

This invention also provides vector and protein compositions useful for the preparation of medicaments which can be used for preventing or inhibiting apoptosis, maintaining cellular function and viability in a suitable cell or for the treatment of a disease characterized by the unwanted death of target cells.

It also is intended that the compositions and methods of this invention be combined with other suitable compositions and therapies such as the use of CrmA, anti-idiotypic TCR antibodies, antagonists and Fas-receptor.

Experimental Procedures

Experiment I

Analysis of Apoptosis—Apoptosis was assessed by the use of fluorescent DNA-staining dyes to reveal nuclear morphology and by transmission electron microscopy. For propidium iodide staining, MCF7 cells were grown on 22 mm$^2$ No. 1 glass coverslips (Corning) placed in 35 mm wells of a 6-well culture dish (Costar). Following treatment with TNF, anti-Fas cycloheximide (CHX), or no treatment, medium was removed and the wells were rinsed twice with phosphate buffered saline (PBS), fixed in 100% methanol at −20° C. for 10 minutes, washed three times with PBS, and stained at room temperature for 10 minutes in a 100 μg/ml solution or propidium iodide (Sigma) made in PBS. The coverslips were then washed three times with PBS, blotted dry and mounted onto glass slides using Vectashield mounting medium for fluorescence (Vector Laboratories). BJAB cells were stained using acridine orange (Sigma) by preparing a wet mount of 30 μl of a cell suspension at a density of approximately 3×10$^5$ cell/ml mixed with 5 μl of a 100 μg/ml acridine orange solution made in PBS. Both propidium iodide-stained MCF7 and acridine orange-stained BJAB nuclei were visualized by fluorescence microscopy using a FITC range barrier filter cube. Laser-scanning confocal microscopy was performed using the Bio-Rad MRC 600 confocal microscope and digitized images obtained were artificially colorized.

For electron microscopy, cells were fixed and processed as per standard electron microscopy procedures.

Experiment II

Quantitative Apoptosis Assays—MCF7 cells or derived transfectants were plated at a concentration of 2.5×10$^5$ cells/well onto glass coverslips. Two days later, after the cells had adhered and spread, TNF or anti-Fas+CHK were added. TNF was added at a final concentration of 20 ng/ml, anti-Fas at 25 ng/ml, and CHX (Sigma) at 10 μg/ml. After 22 hours for the TNF treated samples or after 18 hours for the anti-Fas+CHX treated samples, cells were fixed, stained with propidium iodide and mounted as described above. Apoptotic and non-apoptotic cells were quantitated based on nuclear morphology using fluorescence microscopy and the percentage of non-apoptotic cells was calculated. A minimum of 100 cells was counted for each sample, and each experiment was done at least in duplicate. Since a small fraction of cells in any normally growing cell culture is undergoing apoptosis, spontaneous apoptosis in untreated or CHX along treated samples was also quantitated. The percentage of non-apoptotic cells in the TNF or anti-Fas+CHX treated samples was then normalized by correcting for the frequency of spontaneous apoptosis in the untreated or CHX alone samples, respectively.

BJAB cells were grown at 3×10$^5$ cells/ml and treated with anti-Fas antibody at a concentration of 250 ng/ml (unless indicated otherwise) for 18 hours after which an aliquot was stained with acridine orange as described above. Apoptotic cells and non-apoptotic cells were quantitated and normalized to untreated samples. Assays were done at least in duplicate.

Secondary assays of cell death used were the MTT conversion assay (as described in Opipari, A. W. et al. *J. Biol. Chem.* (1992) 267:12424–12427) and crystal violet staining and were done as described in Tartaglia, L. A. et al. (1993) *Cell* 74:845–853.

Plasmids, Transfections and Selection of Stably Transfected Lines—The crmA gene as shown FIG. 8 and the mutant form were separately cloned into the pcDNA3 (Invitrogen) mammalian expression vector. The CrmA gene was obtained from Dr. David Pickup (Duke University) and used as a template in a PCR reaction using custom oligonucleotide primers with built-in restriction enzyme sites to amplify the entire coding sequence. The sequence of the primers are:

crmA/5'/R1
5' CAC, CGG AAT TCC ACC ATG GAT ATC TTC AGG GAA ATC G (SEQ ID NO: 1)

crmA/3'/XbaI
5' GCT CTA GAC TCG AGT TAA TTA GTT GTT GGA GAG CAA TAT C (SEQ ID NO: 2)

This PCR fragment was digested with EcoR1 and Xba1 restriction enzymes and subcloned into the pcDNA3 vector which had been similarly digested. Following transformation into competent XL-1Blue host *E. coli* cells (Stratagene), individual colonies were grown up, plasmid extracted and the presence of the crmnA gene confirmed by both restriction mapping and DNA sequence analysis.

The resulting expression construct or pcDNA3 itself (as the control) was introduced into both MCF7 and BJAB cells by electroporation. MCF7 cells were electroporated at 330 V, 960 μF in 0.4 cm cuvettes (BioRad), plated onto 100 mm dishes at varying dilutions and selected with G418 sulfate (Gibco-BRL) at a concentration of 500 μg/ml. After selection for three weeks, pooled populations from each transfection were prepared by trypsinizing dishes containing several hundred colonies. Additionally, clonal cells lines were derived by picking individual colonies from selected dishes. BJAB cells were electroporated at 220 V, 960 μF in 0.4 cm cuvettes (Bio-Rad) and selected in 3 mg/ml G418 sulfate. One day following transfection, a portion of the cell population was diluted at a concentration of 2500 cells/well in 96-well dishes from which clonal lines were obtained after G418 selection. The remainder of the cells were retained as the pooled population.

Experiment III

Cell Lines, TNF and Anti-Fas Antibody—The MCF7 cell line was a TNF-sensitive subclone obtained from Dr. David R. Spriggs (University of Wisconsin). MCF7 is a breast carcinoma epithelial cell line which expresses TNF receptor and is sensitive to TNF killing. The BJAB cell line was a gift of Dr. Fred Wang (Harvard). Recombinant TNF (specific activity 6.27×10$^7$ U/mg) was obtained from Genentech (South San Francisco, CA). Anti-Fas monoclonal antibody (clone CH-11, IgM) was obtained from Pan Vera (Madison, Wis.).

Experiment IV

RNA Isolation and Northern Analysis of CrmA—RNA isolation and northern analysis were carried out as described in Dixit et al. (1990) *J. Biol Chem.* 265:2973–2978. PCR (Perkin-Elmer) was used to generate a probe spanning the coding region of the crmA gene as described above. β-actin cDNA probe was purchased from Clontech (Palo Alto, Calif.) and the hybridization signal was visualized as a digitized image on a Molecular Dynamics Phosphorimager.

Experiment IV

Induction of Apoptosis by TNF and anti-Fas—A subclone of the MCF7 breast carcinoma epithelial cell line which expressed TNF receptor and was sensitive to TNF killing was chosen for these studies. This cell line is characterized in Spriggs et al. (1988) *J. Clinc. Invest.*, 81:455–460. Further analysis revealed that Fas was also expressed on these cells and that crosslinking with an anti-Fas monoclonal antibody in the concomitant presence of the protein synthesis inhibitor cycloheximide induced cell death.

Cycloheximide alone for the duration of the assay did not induce cell death beyond the negligible frequency of spontaneous apoptosis which is observed in any untreated cell culture. Anti-Fas alone was not cytotoxic, but this is not surprising, since induction of cell death in non-lymphoid cells by Fas activation has been reported to require the concomitant presence of either transcriptional or translational inhibitors. See Itoh et al. (1991) *Cell* 66:233–243.

A B-cell lymphoma cell line (BJAB) also was examined. It expresses a high level of Fas and was killed by the addition of anti-Fas antibody in the absence of a protein synthesis inhibitor.

Cell death can occur by two biochemically and morphologically distinct processes: apoptosis and necrosis. In these studies, cell death was first confirmed to be the result of TNF or anti-Fas induced apoptosis, not necrosis. Although various markers of apoptosis have been reported, the phenomenon is preferably defined at the morphological level and is characterized by chromatin condensation and margination along the inner nuclear membrane, cytoplasmic condensation and membrane blebbing without disintegration of the cellular membrane. See Duvall et al. (1986) *Immunol. Today* 7:115–119. Conversely necrosis is defined by cytoplasmic swelling and lysis of the cell membrane and, importantly, does not exhibit the chromatin margination characteristic of apoptosis. DNA laddering, representative of cleavage at internucleosomal intervals, is seen in some but not all forms of apoptosis, further emphasizing the importance of morphological criteria in defining apoptosis. See Barres et al. (1992) *Cell* 70:31–46. Nuclear morphology of cells dying in response to TNF or anti-Fas antibody was examined following staining with the DNA-binding dyes propidian iodine (MCF7 cells) and acridine orange (BJAB cells). Fluorescence microscopy laser scanning confocal microscopy demonstrated marked changes in nuclear morphology in the MCF7 cells in response to either TNF or anti-Fas-CHX and in the BJAB cells in response to anti-Fas. Chromatin condensation was clearly visible by immunofluorescence microscopy in both cell lines and formed the basis for the later assays of apoptosis in transfected cell lines. Confocal microscopy confirmed margination along the inner nuclear membrane. These morphological criteria of apoptotic cell death were further confirmed by transmission electron microscopy. The MCF7 cells clearly demonstrated chromatin condensation and margination along the inner nuclear membrane, cytoplasmic condensation and increased membrane blebbing in response to either TNF or anti-Fas+ CH. BJAB cells treated with anti-Fas antibody demonstrated chromatin margination and cellular shrinkage typical of apoptosis in lymphoid cells. Thus, both TNF and Fas induced genuine apoptotic cell death in these cell lines.

Experiment V

Cloning of a cDNA encoding Yama—The cDNA clone (b4HB3MA-COT8-HAP-Ft280 5') corresponding to EST T10341 was kindly provided by M. Bento Soares (Columbia University) and used to screen a random-primed cDNA library constructed from human umbilical vein endothelial cells treated with TNF and cycloheximide. Double-stranded DNA sequencing revealed an open reading frame, designated Yama, of 277 amino acids.

Experiment VI

Expression and purification of 6xHis-tagged Yama—A 2.3 kb Nco 1/Bam Hi fragment from the Yama cDNA described above was ligated into a vector (pTM1) that contained an N-terminal $His_6$ fusion to facilitate purification. This construct contained the 6xHis tag followed by the complete coding region of Yama along with 1800 bp of 3' untranslated DNA. Coupled transcription/translation was performed with the TNT® kit (Promega) according to the manufacturer's recommendations with modifications. Briefly, 4 µg of plasmid DNA was incubated for 1 hour at 31° C. in a total volume of 400 µl containing the kit reaction mixes and 160 µCi of translation grade [$^{35}$S]Met. The translation reaction was diluted 1:20 with 20 mM Hepes buffer, pH 7.4, loaded onto an equilibrated 500 µl DEAE sepharose (Pharmacia) column, then washed with 8 ml of Hepes buffer. The column was eluted with 5 ml of 20 mM Hepes, 0.5M NaCl. This eluate was loaded onto a 300 µl Ni-NTA column (Qiagen), then washed with 5 ml of Reaction Buffer (50 mM Hepes pH 7.4, 0.1 M NaCl, 0.1% CHAPS, and 10% sucrose). The protein was eluted with 5×400 µl fractions of Reaction Buffer with 50 mM imidazole.

Experiment VII

Activation of Yama and in vitro reconstitution experiments—Purified Yama (20 µl) was activated by incubating at 37° C. for 4 hours with 1.5 pmol ICE in Reaction Buffer supplemented with DTT (10 mM) in a total volume of 25 µl, after which 30 µl of Reaction Buffer was added and the reaction incubated at 37° C. for an additional 15 minutes. Following activation, 30 µl of either control Reaction Buffer or Reaction Buffer containing 270 pmol recombinant 6xHis-CrmA or 270 pmol recombinant 6xHisCrmA-mutant was added and allowed to incubate at 37° C. for 30 minutes. The recombinant proteins as well as the control buffer had been pre-incubated with DTT (2 mM) to pre-activate CrmA. Following the 30 minute incubation, 2 µl (0.586 µg) purified PARP was added and the DTT concentration raised to 10 mM, following which the reaction was allowed to proceed for 2 hours at 37° C. The PARP alone control reaction was carried out under identical conditions, except that no Yama, ICE, or CrmA proteins were added during the procedure. The ICE+PARP reaction was carried out identically as well, except that no Yama or CrmA proteins were added during the procedure.

Following the incubation with PARP, one-fifth of each reaction sample was analyzed by immunoblotting using anti-PARP monoclonal antibody C-2-10 as described later. Additionally, an equivalent amount of each sample was resolved by SDS-PAGE and analyzed using a Molecular Devices Phosphorimager to assess the state of radiolabeled Yama present in the reaction. Purified ICE was a gift of Nancy Thornberry (Merck). PARP was purified as has been described in Zahradka and Ebisuzaki (1984) *Eur. J. Biochem.* 142:503–509.

Experiment VIII

CrmA immunoprecipitation to detect complex formation with Yama—Reactions were assembled by combining 20 µl of [$^{35}$S]-Met-labeled pro-Yama or ICE-activated Yama with either 358 pmol native CrmA or 358 pmol mutant CrmA protein. Each reaction was diluted to a final volume of 80 µl in Reaction Buffer. Complex formation was allowed to occur at 37° C. for 30 minutes. Ten (10) µl of each reaction was resolved by SDS-PAGE and subjected to phosphorimaging to visualize the radiolabeled Pro-Yama or activated Yama. Thirty-five (35) μl of each reaction was diluted to 1 ml in PBS-TDS (as described in O'Rourke et al. (1992) *J. Biol. Chem.* 267:24921–24924) and immunoprecipitated using 25 μl of the rabbit polyclonal CrmA antiserum (described later in this section). Immunoprecipitation was carried out as described in O'Rourke et al. (1992) supra and precipitates were resolved by SDS-PAGE and subjected to phosphorimaging analysis to detect the presence of radiolabeled Pro-Yama or activated Yama. Coomassie blue staining of the gel revealed that equivalent amounts of native CrmA and mutant CrmA were precipitated by the CrmA antiserum.

Experiment IX

Generation of CrmA-mutant plasmids for eukaryotic, bacterial and in vitro expression—A four-primer PCR-based method (as described in Higuchi et al. (1988) *Nucleic Acids Res.* 16:7351–7367) was employed to convert codon 291 in the CrmA gene from Thr to Arg (SEQ ID NO: 3 and (SEQ ID NO: 4). The wild-type sequence of the cDNA and protein are shown in FIG. 8. Initially, two independent PCR reactions were performed using the plasmid pcDNA3/CrmA (as described in Tewari and Dixit (1995) *J. Biol. Chem.* 270:3255–3260) and Experiment II, above) as template. One reaction consisted of an upstream primer (Primer A) corresponding to nucleotides 682–711 of the CrmA coding sequence (with nucleotide 1 representing the first nucleotide of the initiator methionine codon), and a downstream mutagenic primer (Primer M2) complementary to nucleotides 853–896. Primer M2 contained a G to A transition which eliminated a Pst 1 site and base changes which altered codon 291 to encode Arg instead of Thr and, additionally, introduced a diagnostic Nru 1 site. The second PCR reaction used an upstream sense mutagenic primer (Primer M1) complementary to primer M2 and a downstream primer (Primer B) complementary to the last 26 nucleotides of the CrmA coding region with custom Xba 1 and Xho 1 sites. The PCR products were gel purified, combined, denatured by boiling and annealed by slow cooling to room temperature. Following a 10 minute extension reaction, PCR was carried out using the flanking primers A and B. The amplification product was digested with Cla 1 (cuts at nucleotide 692 in the CrmA coding sequence) and Xba 1 and cloned into pcDNA3/CrmA which had been similarly digested. The mutation was verified by DNA sequencing, as were all segments derived by PCR amplification. This recombinant plasmid was designated pcDNA3/CrmA-mutant.

The sequences of oligonucleotide primers were as follows: Primer A. 5' GCT ATG TTT ATC GAT GTG CAC ATT CCC AAG; (SEQ ID NO: 9) Primer M2: 5' GCA CAA GTT GCT GCG GCT GCT TCG CGA TAC TCT TCA TTG ACA TC; (SEQ ID NO: 10) Primer B, 5' GCT CTA GAC TCG AGT TAA TTA GTT GTT GGA GAG CAA TAT C; (SEQ ID NO: 11) Primer M1, 5' GAT GTC AAT GAA GAG TAT CGC GAA GCA GCC GCA GCA ACT TGT GC (SEQ ID NO: 12).

For purposes of in vi tro transcription and translation, the native CrmA gene and its mutant version were digested with Nco 1 and Xho 1 and ligated into a plasmid based on pTM1 (Moss et al. (1990) *Nature* 348:91–92) that encoded an in-frame N-terminal Met-His$_6$ tag to facilitate purification. The coding sequence started with the initiator methionine, followed by six histidines, a serine and then the entire coding region of CrmA or the mutant.

For expression in *E. coli*, the native and mutant CrmA genes in pTM1 were digested with Nco 1 and Xho 1 and ligated into a derivative of the isopropyl-1-thio-β-D-galactopyranoside (IPTG)-inducible plasmid pFLAG (IBI) that contained the same His$_6$ fusion tag. Additionally, the CrmA gene from pcDNA3/CrmA (Tewari and Dixit (1995) supra was subcloned into the Nco 1/Xho 1 digested pGSTag bacterial expression vector (provided by Dr. Holly Dressler, a Massachusetts General Hospital and described in Ron and Dressler (1992) *BioTechniques* 13:866–869) generating a chimeric glutathione-S-transferase (GST)-CrmA open reading frame.

Experiment X

Preparation of GST-CrmA fusion protein and generation of rabbit polyclonal antiserum—Antibodies were raised against recombinant CrmA fusion proteins. Initial immunization was with the 6xHis-tagged CrmA recombinant protein and subsequent immunizations were with a GST-CrmA fusion protein produced as described previously (Hu et al. (1994) *J. Biol. Chem.* 269:30069–30072). Briefly, the BL2lpLyS *E. coli* strain was transformed with pGSTag-CrmA plasmid and production of fusion protein induced in culture by the addition of IPTG to 50 μM. Following a 1.5 hour incubation at 25° C., the cells were recovered by centrifugation, resuspended in lysis buffer (20 mM Tris pH 8.0, 0.5 M NaCl, 10% glycerol, 1 mM PMSF, 1 mg/ml leupeptin, 1 mg/ml aprotinin, 10 mg/ml soybean trypsin inhibitor, 1 mg/ml pepstatin and 0.1% Triton X-100), sonicated, clarified by centrifugation, and absorbed to glutathione-agarose beads (Sigma). Soluble GST-CrmA fusion protein was eluted by incubating with 5 mM free glutathione (Sigma). Typical yield of fusion protein was 1 mg per liter of bacterial culture. Immunization of rabbits and screening of antisera was as previously described (O'Rourke et al. (1992) *J. Biol. Chem.* 267:24921–24924).

Experiment XI

Expression and purification of recombinant 6xHis-tagged CrmA proteins from *E. coli*—*E. coli* strain TG1 transformed with either the 6xHisCrmA or 6xHisCrmA-mutant construct was induced with IPTG for 3 hours, harvested and the cells lysed by sonication was pelleted by centrifugation. The supernatant contained soluble CrmA was filtered through a 0.22 pm filter, loaded onto a 2 ml Ni-NTA column (Qiagen), and washed with 50 mM Tris pH 8.0 containing 0.5 M NaCl. CrmA was eluted with 50 mM Tris, 50 mM imidazole pH 8.0, containing 0.1 M NaCl. This material was diluted with 9 volumes of 20 mM Hepes pH 7.4 containing 2 mM dithiothreitol and applied to a 2 ml column of DEAE Sepharose. This column was developed with a linear gradient of 0–1 M NaCl in 20 mM Herpes buffer, pH 7.4, and CrmA eluted at approximately 0.4 M NaCl to give a yield of 4 mg protein from six liters of culture. The material was greater than 95% pure as estimated by Coomassie blue staining and was stored at −70° C. until use. In all experiments using this material, the CrmA was treated with 2 mM DTT for 5 minutes immediately before use. This resulted in CrmA with the highest inhibitory activity.

Experiment XII

In vitro assay of ICE inhibition by recombinant CrmA or CrmA-mutant protein—To assay for inhibition, 44 ng of purified ICE was activated with 10 mM DTT for five minutes at room temperature, then incubated at 37° C. with various amounts of purified CrmA or CrmA-mutant protein in a total volume of 95 μl of reaction buffer: 20 mM Hepes buffer, pH 7.4, containing 100 mM NaCl, 0.5% NP40, and 10 mM DTT. After 15 minutes, 5 µl of a 10 mM stock in DMSO of Boc-Ala-Ala-Pro-Asp-p-nitroanilide was added to determine the residual ICE activity by observing the release of p-nitroaniline at 410 nm using a Molecular Devices $V_{max}$ plate reader operating in the kinetic mode. The data were expressed as the reaction velocity in the presence of inhibitor $(v_i)$ divided by the velocity in its absence $(v_o)$, which represents residual ICE activity. The data represent the mean and standard deviations of values derived from two independent experiments. Purified recombinant human ICE was supplied by Nancy Thornberry (Merck).

Experiment XIII

In vitro transcription/translation of CrmA and CrmA-mutant—Coupled transcription/translation was performed using the TNT® kit from Promega according to the manufacturer's recommendations. Briefly, 0.5 µg of plasmid DNA was incubated for one hour at 31° C. in a total volume of 50 µl containing the kit reagents and 20 µCi of translation grade [$^{35}$S] Met. Once translated, the reaction mix was either used immediately or stored at –20° C. until needed.

Experiment XIV

Gel-Shift assays to detect complex formation between ICE and CrmA or CrmA-mutant—Serpin reactions with target proteases can be analyzed by gel-shift analysis using purified proteinases and [$^{35}$S] Met labelled serpins produced by in vitro translation, as described in Komiyama et al. (1994) "Techniques in Protein Chemistry" Acad. Press, San Diego, Calif., pp. 305–312 and Komiyama et al. (1994) *J. Biol. Chem.* 269:19331–19337. In-vitro transcribed and translated CrmA or CrmA-mutant was diluted with an equal volume of 50 mM Hepes buffer pH 7.4 containing 100 mM NaCl, 10% sucrose, and 0.1% CHAPS. 10 µl of the diluted lysates were incubated with 10 µl of consecutive three-fold dilutions of ICE in the same buffer containing 10 mM DTT for 30 minutes at 37° C. Samples were then resolved by native gel electrophoresis and visualized using a Molecular Devices Phosphorimager.

Experiment XV

Transverse Urea Gradient PAGE—In vitro translated CrmA or CrmA-mutant protein was subjected to electrophoresis in transverse urea gradient (TUG) polyacrylamide gels (0 to 8 M) as previously described in Goldenberg (1989) "Protein Structure: A Practical Approach" IRL Press, N.Y. pp. 225–250 and Mast et al. (1991) *Biochem.* 30:1723–1730. The gels were dried and analyzed using a Molecular Devices Phosphorimager.

Experiment XVI

Stable transfection of BJAB and MCF7 cells—MCF7 or BJAB cells were electroplated with pcDNA3/CrmA-mutant plasmid and stable clonal cell lines generated as previously described (Tewari and Dixit (1995) supra and Experiment II).

MCF7 cells, BJAB cells and derived vector and CrmA stable transfectants, along with CrmA-mutant transfected stable lines generated in this study were maintained in RPMI-1640 medium supplemented with 10% heat-inactivated fetal bovine serum (Hyclone), L-glutamine, penicillin/streptomycin, nonessential amino acids and additionally supplemented with G418 sulfate (Gibco-BRL/Life Technologies, Inc.) to 500 µg/ml for MCF7 transfectants and 3 mg/ml for BJAB transfectants.

Experiment XVII

Treatment with Anti-Fas or TNF and Preparation of Cell Lysates for PARP Analysis—MCF7 cells or derived transfectants were plated in 100 mm dishes at a concentration of $2 \times 10^6$ cells per dish. On the second day, cells were treated with TNF at 40 ng/ml for the indicated time periods. Following a PBS rinse, cells were harvested by scraping into 15 ml PBS+Protease Inhibitors (1 mM PMSF, 0.5 mg/ml aprotinin, 0.5 mg/ml antipain, and 0.5 mg/ml pepstatin), recovered by centrifugation and lysed in 2.5 ml Sample Buffer (50 mM Tris-HCl, pH 6.8. 6 M urea, 6% 2-mercaptoethanol, 3% SDS and 0.003% bromophenol blue). In cases where nonadherent cells were present in the culture medium (e.g., at later time points), floating cells were also harvested by centrifugation and combined with the adherent cell pellet before lysis in Sample Buffer.

BJAB cells or derived transfectants were aliquoted at a concentration of $5 \times 10^5$/ml into six-well dishes, with 4 ml in each well. The following day, cells were treated with anti-Fas antibody (250 ng/ml) for the indicated time periods, harvested by centrifugation, washed once with PBS+Protease Inhibitors and lysed in 2 ml Sample Buffer.

For detection of CrmA, whole cell lysates ($2 \times 10^5$ cells per lane) were resolved by SDS-PAGE, transferred to nitrocellulose and processed as previously described (Shao et al. 1994). The ant-GST-CrmA rabbit antiserum was used at a dilution of 1:1,000 and a horseradish peroxidase-conjugated donkey anti-rabbit secondary antibody (Amersham Life Sciences) used at a 1:15,000 dilution. Visualization of signal was by ECL (Amersham).

Immunoblotting of lysates for PARP was carried out as described in Desnoyers et al. (1994) *Anal. Biochem.* 218:470–473. The anti-PARP mouse monoclonal antibody was used at a dilution of 1:10,000 and the secondary antibody, an anti-mouse Ig labeled with horseradish peroxidase, was used at a dilution of 1:1,000. Visualization of signal was also by ECL.

Experiment XVIII

TNF, Anti-Fas Antibody and Anti-PARP Antibody—Recombinant TNF (specific activity $6.27 \times 10^7$ U/mg) was a gift from Genentech (South San Francisco, Calif.). Anti-Fas monoclonal antibody (clone CH-11, IgM) was obtained from PanVera (Madison, Wis.). The anti-PARP monoclonal antibody was clone C-2-10, which, as described previously (Lamarre et al. (1988) *Biochem. Biophys. Acta.* 950:147–160, recognizes an epitope near the N-terminal end of PARP, located between amino acids 216 and 375.

Experimental Results and Discussion

A human umbilical vein endothelial cell library was screened from which a cDNA encoding an open reading frame of 277 amino acids, designated Yama was cloned. Yama is homologous to the Ced-3/ICE family of proteins. Yama was then assayed for protease activity and to determine if it fulfilled the requirements predicted for a death protease. The amino acid sequence suggested that it would be an Asp-specific cysteine protease, as the residues thought to be important for Asp-specificity in ICE are conserved in Yama. Yama was expressed in vitro as a fusion to a GxHis purification tag at the N-terminus and isolated by ion exchange and nickel chelate affinity chromatography to determine if it possessed proteolytic activity capable of cleaving PARP. The full-length, p32 form of purified Yama had no proteolytic activity against PARP (FIG. 2A, Top, Lane 3) and is thus designated Pro-Yama. Purified ICE was able to cleave Pro-Yama to yield two major products (FIG. 2A, Bottom, Lane 4; putative p20 and p11 subunits are indicated by open arrows) and, more importantly, that Yama activated in this manner acquired proteolytic activity and cleaved PARP to the 85 kDa apoptotic form (FIG. 2A, Top, Lane 4). Purified ICE did not cleave PARP (FIG. 2A, Top, Lane 2), confirming the earlier results of Lazebnik et al. (1994) *Nature* 371:346–347, and excluding the possibility that PARP cleavage was mediated by the added ICE. The next investigation concerned whether PARP cleavage occurred in these cells death systems and whether the cleavage product was analogous to that observed in the in vitro experiments. Activation of either Fas (in BJAB lymphoma cells) or TNF receptors (in MCF7 breast carcinoma cells) induced PARP cleavage to the signature 85 kDa form (FIG. 2B), and this product co-migrated with the PARP cleavage fragment generated by purified Yama (FIG. 2A, Top, Lanes 4 and 5). Thus, Yama is a protease which cleaves PARP to the signature 85 kDa apoptotic fragment.

Since the mammalian cell death protease is expected to be susceptible to inhibition by CrmA, whether Yama was CrmA-inhibitable was then investigated. To address this question definitively, purified proteins were used to reconstitute the PARP cleavage reaction in vitro such that purified recombinant CrmA protein could be added. To serve as a control, a point mutant of CrmA was constructed. CrmA-mutant carries a single amino acid substitution of Arg for Thr at amino acid 291 (FIG. 3A). Both CrmA and CrmA-mutant proteins were expressed as 6xHis-tag fusion proteins in *E. coli* and purified by nickel chelate affinity chromatography. In vitro characterization of the CrmA-mutant protein revealed that under conditions where CrmA bound and inhibited ICE, the mutant protein neither bound ICE (FIG. 3B) nor inhibited its proteolytic activity (FIG. 3A). The tertiary structure of CrmA-mutant, however, was not significantly altered by the point mutation, as its conformational signature was indistinguishable from that of wild-type CrmA on transferase urea gradient PAGE (FIG. 3C), a method used to probe the tertiary structures of serpins (Goldenberg (1989) supra; Mast et al. (1991) supra; and Komiyama et al. (1994) supra).

Using these purified recombinant proteins, CrmA markedly inhibited the cleavage of PARP by Yama in vitro (FIG. 4). When CrmA was replaced with an equivalent amount of CrmA-mutant protein, no inhibition of PARP cleavage was observed (FIG. 4), indicting that the effect of CrmA was a function specifically of its ability to act as a protease inhibitor.

To confirm that CrmA directly interacts with Yama, the ability of either Pro-Yama or activated Yama to form a complex with either native CrmA or mutant CrmA was examined. Pro-Yama or activated Yama (both labeled with [31S]-Met) were each incubated with either native CrmA or an equivalent amount of mutant CrmA recombinant protein. Each reaction was subjected to immunoprecipitation analysis using a polyclonal CrmA antiserum and the immunoprecipitates resolved by SDS-PAGE and visualized by phosphorimaging. CrmA associated with the activated two-subunit form of Yama but not with Pro-Yama (FIG. 5B). CrmA-mutant bound neither activated Yama nor Pro-Yama (FIG. 5B). It was determined that CrmA interacts directly with activated Yama to form an inhibitory complex.

Since CrmA inhibited the cleavage of PARP by Yama in vitro, it was inferred that if Yama is indeed responsible for PARP cleavage during apoptosis, then CrmA should inhibit PARP cleavage in vivo. To investigate this, the MCF7 breast carcinoma and BJAB lymphoma cell lines stably transfected with either vector were utilized, CrmA or CrmA-mutant expression constructs. Clonal cell lines which expressed the indicated proteins were selected and protein expression confirmed by immunoblotting using an anti-CrmA polyclonal antiserum (FIG. 6A). In keeping with the in vitro findings, expression of CrmA inhibited proteolytic cleavage of PARP to the signature 85 kDa fragment normally generated during apoptosis induced by either Fas (BJAB cells) or TNF receptors (MCF7 cells), whereas in the vector ad CrmA-mutant lines, cleavage of PARP proceed unabated (FIGS. 6B, 6C).

To investigate whether the in vivo blockage of PARP cleavage by CrmA and lack thereof by CrmA-mutant correlated with the ability of these proteins to inhibit apoptosis, the BJAB and MCF7 transfectants were examined. CrmA afforded protection from TNF-induced apoptosis as expected, whereas CrmA-mutant expressing lines showed no protection and were as sensitive as a vector-transfected line (FIG. 7, bottom). The protection conferred by CrmA and lack thereof by CrmA-mutant was readily apparent on examination of nuclear morphology of propidium-iodide stained cells (FIG. 7, top). When BJAB transfectants were examined for sensitivity to Fas-induced PCD, CrmA was protective whereas CrmA-mutant expression lines remained as sensitive as a vector control line (FIG. 7, bottom). Thus, it was concluded that the divergent abilities of CrmA and CrmA-mutant to block PARP cleavage correlate with the abilities of these proteins to block cell death.

The finding that CrmA inhibits the proteolytic activity of Yama (FIG. 4) is significant, as it shows that the well-documented ability of CrmA to inhibit apoptosis can now be explained by its inhibition of Yama. Also, the finding that CrmA inhibits PARP cleavage in vivo is consistent with its inhibiting Yama.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A composition an isolated and purified nucleic acid, wherein said isolated and purified nucleic acid comprises SEQ ID NO:5.

2. The composition of claim 1, wehrein said isolated and purified nucleic acid further comprises nucleic acid encoding a glutathione-S-tranferase tag.

3. The composition of claim 1, wherein said isolated and purified nucleic acid further comprises nucleic acid encoding a HIS tag.

* * * * *

SEQUENCE LISTING (1) GENERAL INFORMATION:

(iii) NUMBER OF SEQUENCES: 12

```
(2) INFORMATION FOR SEQ ID NO:1:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:1:

CACCGGAATT CCACCATGGA TATCTTCAGG GAAATCG                              37

(2) INFORMATION FOR SEQ ID NO:2:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:2:

GCTCTAGACT CGAGTTAATT AGTTGTTGGA GAGCAATATC                           40

(2) INFORMATION FOR SEQ ID NO:3:

(i) SEQUENCE CHARACTERISTICS:
        (A) LENGTH: 1468 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 295..1317

(ix) FEATURE:
        (A) NAME/KEY: misc_feature
        (B) LOCATION: 1165..1167
        (D) OTHER INFORMATION: /note= "Can also be CGT, CGC, CGA
            or CGG with corresponding amino acid Arginine
            (Mutant crmA)"

(ix) FEATURE:
        (A) NAME/KEY: misc_feature
        (B) LOCATION: 682..711
        (D) OTHER INFORMATION: /note= "Primer A"

(ix) FEATURE:
        (A) NAME/KEY: misc_feature
        (B) LOCATION: 853..896
        (D) OTHER INFORMATION: /note= "Primer M2 and complement of
            of Primer M1"

(ix) FEATURE:
        (A) NAME/KEY: misc_feature
        (B) LOCATION: 1291..1317
        (D) OTHER INFORMATION: /note= "Complement of Primer B"

(xi) SEQUENCE DESCRIPTION: SEQ ID NO:3:

TCCATGGAAG AACGAAAGTA GTATAAAAGT AATAAAACAA AAAAAAGAAT ATAAAAAATT      60

TATAGCCACT TTCTTTGAGG ACTGTTTTCC TGAAGGAAAT GAACCTCTGG AATTAGTTAG     120

ATATATAGAA TTAGTATACA CGCTAGATTA TTCTCAAACT CCTAATTATG ACAGACTACG     180

TAGACTGTTT ATACAAGATT GAAAATATAT TTCTTTTTAT TGAGTGGTGG TAGTTACGGA     240

TATCTAATAT TAATATTAGA CTATCTCTAT CGTCACACAA CAAAATCGAT TGCC ATG       297
                                                            Met
                                                             1

GAT ATC TTC AGG GAA ATC GCA TCT TCT ATG AAA GGA GAG AAT GTA TTC       345
Asp Ile Phe Arg Glu Ile Ala Ser Ser Met Lys Gly Glu Asn Val Phe
          5                  10                 15
```

-continued

| | |
|---|---|
| ATT TCT CCA CCG TCA ATC TCG TCA GTA TTG ACA ATA CTG TAT TAT GGA<br>Ile Ser Pro Pro Ser Ile Ser Ser Val Leu Thr Ile Leu Tyr Tyr Gly<br>        20                      25                    30 | 393 |
| GCT AAT GGA TCC ACT GCT GAA CAG CTA TCA AAA TAT GTA GAA AAG GAG<br>Ala Asn Gly Ser Thr Ala Glu Gln Leu Ser Lys Tyr Val Glu Lys Glu<br>35                      40                      45 | 441 |
| GCG GAC AAG AAT AAG GAT GAT ATC TCA TTC AAG TCC ATG AAT AAA GTA<br>Ala Asp Lys Asn Lys Asp Asp Ile Ser Phe Lys Ser Met Asn Lys Val<br>50                      55                    60               65 | 489 |
| TAT GGG CGA TAT TCT GCA GTG TTT AAA GAT TCC TTT TTG AGA AAA ATT<br>Tyr Gly Arg Tyr Ser Ala Val Phe Lys Asp Ser Phe Leu Arg Lys Ile<br>        70                      75                    80 | 537 |
| GGA GAT AAT TTC CAA ACT GTT GAC TTC ACT GAT TGT CGC ACT GTA GAT<br>Gly Asp Asn Phe Gln Thr Val Asp Phe Thr Asp Cys Arg Thr Val Asp<br>              85                      90                    95 | 585 |
| GCG ATC AAC AAG TGT GTT GAT ATC TTC ACT GAG GGG AAA ATT AAT CCA<br>Ala Ile Asn Lys Cys Val Asp Ile Phe Thr Glu Gly Lys Ile Asn Pro<br>            100                    105                  110 | 633 |
| CTA TTG GAT GAA CCA TTG TCT CCA GAT ACC TGT CTC CTA GCA ATT AGT<br>Leu Leu Asp Glu Pro Leu Ser Pro Asp Thr Cys Leu Leu Ala Ile Ser<br>115                      120                    125 | 681 |
| GCC GTA TAC TTT AAA GCA AAA TGG TTG ATG CCA TTT GAA AAG GAA TTT<br>Ala Val Tyr Phe Lys Ala Lys Trp Leu Met Pro Phe Glu Lys Glu Phe<br>130                      135                    140               145 | 729 |
| ACC AGT GAT TAT CCC TTT TAC GTA TCT CCA ACG GAA ATG GTA GAT GTA<br>Thr Ser Asp Tyr Pro Phe Tyr Val Ser Pro Thr Glu Met Val Asp Val<br>                  150                    155                  160 | 777 |
| AGT ATG ATG TCT ATG TAC GGC GAG GCA TTT AAT CAC GCA TCT GTA AAA<br>Ser Met Met Ser Met Tyr Gly Glu Ala Phe Asn His Ala Ser Val Lys<br>            165                    170                  175 | 825 |
| GAA TCA TTC GGC AAC TTT TCA ATC ATA GAA CTG CCA TAT GTT GGA GAT<br>Glu Ser Phe Gly Asn Phe Ser Ile Ile Glu Leu Pro Tyr Val Gly Asp<br>        180                    185                    190 | 873 |
| ACT AGT ATG GTG GTA ATT CTT CCA GAC AAT ATT GAT GGA CTA GAA TCC<br>Thr Ser Met Val Val Ile Leu Pro Asp Asn Ile Asp Gly Leu Glu Ser<br>195                      200                    205 | 921 |
| ATA GAA CAA AAT CTA ACA GAT ACA AAT TTT AAG AAA TGG TGT GAC TCT<br>Ile Glu Gln Asn Leu Thr Asp Thr Asn Phe Lys Lys Trp Cys Asp Ser<br>210                      215                    220               225 | 969 |
| ATG GAT GCT ATG TTT ATC GAT GTG CAC ATT CCC AAG TTT AAG GTA ACA<br>Met Asp Ala Met Phe Ile Asp Val His Ile Pro Lys Phe Lys Val Thr<br>                  230                    235                  240 | 1017 |
| GGC TCG TAT AAT CTG GTG GAT GCG CTA GTA AAG TTG GGA CTG ACA GAG<br>Gly Ser Tyr Asn Leu Val Asp Ala Leu Val Lys Leu Gly Leu Thr Glu<br>            245                    250                  255 | 1065 |
| GTG TTC GGT TCA ACT GGA GAT TAT AGC AAT ATG TGT AAT TCA GAT GTG<br>Val Phe Gly Ser Thr Gly Asp Tyr Ser Asn Met Cys Asn Ser Asp Val<br>        260                    265                  270 | 1113 |
| AGT GTC GAC GCT ATG ATC CAC AAA ACG TAT ATA GAT GTC AAT GAA GAG<br>Ser Val Asp Ala Met Ile His Lys Thr Tyr Ile Asp Val Asn Glu Glu<br>275                      280                    285 | 1161 |
| TAT ACA GAA GCA GCT GCA GCA ACT TGT GCG CTG GTG GCA GAC TGT GCA<br>Tyr Thr Glu Ala Ala Ala Ala Thr Cys Ala Leu Val Ala Asp Cys Ala<br>290                      295                    300               305 | 1209 |
| TCA ACA GTT ACA AAT GAG TTC TGT GCA GAT CAT CCG TTC ATC TAT GTG<br>Ser Thr Val Thr Asn Glu Phe Cys Ala Asp His Pro Phe Ile Tyr Val<br>                  310                    315                  320 | 1257 |
| ATT AGG CAT GTC GAT GGC AAA ATT CTT TTC GTT GGT AGA TAT TGC TCT<br>Ile Arg His Val Asp Gly Lys Ile Leu Phe Val Gly Arg Tyr Cys Ser<br>            325                    330                  335 | 1305 |

```
CCA ACA ACT AAT TAAATCACAT TCTTAATATT AGAATATTAG AATATTATAT        1357
Pro Thr Thr Asn
        340

AGTTAAGATT TTTACTAATT GGTTAACCAT TTTTTTAAAA AAATAGAAAA AAAACATGTT   1417

ATATTAGCGA GGGTCGTTAT TCTTCCAATT GCAATTGGTA AGATGACGGC C            1468
```

(2) INFORMATION FOR SEQ ID NO:4:

(i) SEQUENCE CHARACTERISTICS:
        (A) LENGTH: 341 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Ile Phe Arg Glu Ile Ala Ser Ser Met Lys Gly Glu Asn Val
 1               5                  10                  15

Phe Ile Ser Pro Pro Ser Ile Ser Ser Val Leu Thr Ile Leu Tyr Tyr
                20                  25                  30

Gly Ala Asn Gly Ser Thr Ala Glu Gln Leu Ser Lys Tyr Val Glu Lys
            35                  40                  45

Glu Ala Asp Lys Asn Lys Asp Asp Ile Ser Phe Lys Ser Met Asn Lys
        50                  55                  60

Val Tyr Gly Arg Tyr Ser Ala Val Phe Lys Asp Ser Phe Leu Arg Lys
65                  70                  75                  80

Ile Gly Asp Asn Phe Gln Thr Val Asp Phe Thr Asp Cys Arg Thr Val
                85                  90                  95

Asp Ala Ile Asn Lys Cys Val Asp Ile Phe Thr Glu Gly Lys Ile Asn
            100                 105                 110

Pro Leu Leu Asp Glu Pro Leu Ser Pro Asp Thr Cys Leu Leu Ala Ile
        115                 120                 125

Ser Ala Val Tyr Phe Lys Ala Lys Trp Leu Met Pro Phe Glu Lys Glu
    130                 135                 140

Phe Thr Ser Asp Tyr Pro Phe Tyr Val Ser Pro Thr Glu Met Val Asp
145                 150                 155                 160

Val Ser Met Met Ser Met Tyr Gly Glu Ala Phe Asn His Ala Ser Val
                165                 170                 175

Lys Glu Ser Phe Gly Asn Phe Ser Ile Ile Glu Leu Pro Tyr Val Gly
            180                 185                 190

Asp Thr Ser Met Val Val Ile Leu Pro Asp Asn Ile Asp Gly Leu Glu
        195                 200                 205

Ser Ile Glu Gln Asn Leu Thr Asp Thr Asn Phe Lys Lys Trp Cys Asp
    210                 215                 220

Ser Met Asp Ala Met Phe Ile Asp Val His Ile Pro Lys Phe Lys Val
225                 230                 235                 240

Thr Gly Ser Tyr Asn Leu Val Asp Ala Leu Val Lys Leu Gly Leu Thr
                245                 250                 255

Glu Val Phe Gly Ser Thr Gly Asp Tyr Ser Asn Met Cys Asn Ser Asp
            260                 265                 270

Val Ser Val Asp Ala Met Ile His Lys Thr Tyr Ile Asp Val Asn Glu
        275                 280                 285

Glu Tyr Thr Glu Ala Ala Ala Ala Thr Cys Ala Leu Val Ala Asp Cys
    290                 295                 300

Ala Ser Thr Val Thr Asn Glu Phe Cys Ala Asp His Pro Phe Ile Tyr
```

```
                    305                 310                 315                 320
Val Ile Arg His Val Asp Gly Lys Ile Leu Phe Val Gly Arg Tyr Cys
                325                 330                 335

Ser Pro Thr Thr Asn
            340
```

(2) INFORMATION FOR SEQ ID NO:5:

(i) SEQUENCE CHARACTERISTICS:
        (A) LENGTH: 1158 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 224..226
        (D) OTHER INFORMATION: /note= "Dominant inhibitory
            fragment"

(ix) FEATURE:
        (A) NAME/KEY: misc_feature
        (B) LOCATION: 710..712
        (D) OTHER INFORMATION: /note= "Can also be either ATG,
            GCT, GCC, GCA or GCG"

(xi) SEQUENCE DESCRIPTION: SEQ ID NO:5:

```
GGCACGAGCG GATGGGTGCT ATTGTGAGGC GGTTGTAGAA GAGTTTCGTG AGTGCTCGCA      60

GCTCATACCT GTGGCTGTGT ATCCGTGGCC ACAGCTGGTT GGCGTCGCCT TGAAATCCCA     120

GGCCGTGAGG AGTTAGCGAG CCCTGCTCAC ACTCGGCGCT CTGGTTTTCG GTGGGTGTGC     180

CCTGCACCTG CCTCTTCCCG CATTCTCATT AATAAAGGTA TCCATGGAGA ACACTGAAAA     240

CTCAGTGGAT TCAAAATCCA TTAAAAATTT GGAACCAAAG ATCATACATG GAAGCGAATC     300

AATGGACTCT GGAATATCCC TGGACAACAG TTATAAAATG GATTATCCTG AGATGGGTTT     360

ATGTATAATA ATTAATAATA AGAATTTTCA TAAAAGCACT GGAATGACAT CTCGGTCTGG     420

TACAGATGTC GATGCAGCAA ACCTCAGGGA ACATTCAGA AACTTGAAAT ATGAAGTCAG      480

GAATAAAAAT GATCTTACAC GTGAAGAAAT TGTGGAATTG ATGCGTGATG TTTCTAAAGA     540

AGATCACAGC AAAAGGAGCA GTTTTGTTTG TGTGCTTCTG AGCCATGGTG AAGAAGGAAT     600

AATTTTTGGA ACAAATGGAC CTGTTGACCT GAAAAAAATA ACAAACTTTT TCAGAGGGGA     660

TCGTTGTAGA AGTCTAACTG GAAAACCCAA ACTTTTCATT ATTCAGGCCT GCCGTGGTAC     720

AGAACTGGAC TGTGGCATTG AGACAGACAG TGGTGTTGAT GATGACATGG CGTGTCATAA     780

AATACCAGTG GAGGCCGACT TCTTGTATGC ATACTCCACA GCACCTGGTT ATTATTCTTG     840

GCGAAATTCA AAGGATGGCT CCTGGTTCAT CCAGTCGCTT TGTGCCATGC TGAAACAGTA     900

TGCCGACAAG CTTGAATTTA TGCACATTCT TACCCGGGTT AACCGAAAGG TGGCAACAGA     960

ATTTGAGTCC TTTTCCTTTG ACGCTACTTT TCATGCAAAG AAACAGATTC CATGTATTGT    1020

TTCCATGCTC ACAAAAGAAC TCTATTTTTA TCACTAAAGA AATGGTTGGT TGGTGGTTTT    1080

TTTTAGTTTG TATGCCAAGT GAGAAGATGG TATATTTGGT ACTGTATTTC CCTCTCATTT    1140

GGGCCTACTC TCATGCTG                                                  1158
```

(2) INFORMATION FOR SEQ ID NO:6:

(i) SEQUENCE CHARACTERISTICS:
        (A) LENGTH: 277 amino acids
        (B) TYPE: amino acid
        (C) STRANDEDNESS: single
        (D) TOPOLOGY: linear

```
    (ix) FEATURE:
        (A) NAME/KEY: Modified-site
        (B) LOCATION: 163
        (D) OTHER INFORMATION: /note= "Can be Met or Ala"

(xi) SEQUENCE DESCRIPTION: SEQ ID NO:6:

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
                20                  25                  30

Leu Asp Asn Ser Tyr Lys Met Asp Tyr Pro Glu Met Gly Leu Cys Ile
            35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
                100                 105                 110

Ser Phe Val Cys Val Leu Leu Ser His Gly Glu Glu Gly Ile Ile Phe
            115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
                180                 185                 190

Phe Leu Tyr Ala Tyr Ser Thr Ala Pro Gly Tyr Tyr Ser Trp Arg Asn
            195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
                260                 265                 270

Leu Tyr Phe Tyr His
            275

(2) INFORMATION FOR SEQ ID NO:7:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:7:

Tyr Thr Glu Ala Ala Ala Ala Thr Cys Ala Leu Val Ala Asp
1               5                   10

(2) INFORMATION FOR SEQ ID NO:8:
```

-continued (i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:8:

Tyr Arg Glu Ala Ala Ala Ala Thr Cys Ala Leu Val Ala Asp
1               5                   10

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

GCTATGTTTA TCGATGTGCA CATTCCCAAG                                30

(2) INFORMATION FOR SEQ ID NO:10:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:10:

GCACAAGTTG CTGCGGCTGC TTCGCGATAC TCTTCATTGA CATC                 44

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:11:

GCTCTAGACT CGAGTTAATT AGTTGTTGGA GAGCAATATC                      40

(2) INFORMATION FOR SEQ ID NO:12:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:12:

GATGTCAATG AAGAGTATCG CGAAGCAGCC GCAGCAACTT GTGC                 44